(12) United States Patent
Gallagher et al.

(10) Patent No.: US 9,523,073 B2
(45) Date of Patent: Dec. 20, 2016

(54) ELISA FOR A NATURALLY-OCCURRING SOLUBLE TRUNCATED FORM OF IL-23 RECEPTOR

(75) Inventors: Grant Gallagher, Milltown, NJ (US); Raymond Yu, East Brunswick, NJ (US); Joyce Eskdale, Milltown, NJ (US); Jonathan Brazaitis, Parlin, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 462 days.

(21) Appl. No.: 13/065,867

(22) Filed: Mar. 31, 2011

(65) Prior Publication Data

US 2012/0171704 A1 Jul. 5, 2012

Related U.S. Application Data

(60) Provisional application No. 61/341,457, filed on Mar. 31, 2010, provisional application No. 61/341,165, filed on Mar. 31, 2010.

(51) Int. Cl.
| | |
|---|---|
| *G01N 33/53* | (2006.01) |
| *C12N 5/071* | (2010.01) |
| *C07K 14/715* | (2006.01) |
| *A61K 38/00* | (2006.01) |

(52) U.S. Cl.
CPC ......... *C12N 5/0602* (2013.01); *C07K 14/7155* (2013.01); *A61K 38/00* (2013.01)

(58) Field of Classification Search
None
See application file for complete search history.

(56) References Cited

U.S. PATENT DOCUMENTS

2003/0059871 A1  3/2003  Cosman et al.

OTHER PUBLICATIONS

Kan et al. Locus AM990332, Nov. 1, 2008.*
Oppmann, Lesely B., Immunity, Nov. 2000, 715-725, vol. 13.
Parham, Christi, The Journal of Immunology, 2002, 5699-5708, vol. 168.
Kan, S-H, Genes and Immunity, 2008, 631-639, vol. 9.
Mancini, G., Genes and Immunity, 2008, 555-569, vol. 9.
Aggarwal, Sudeepta, The Journal of Biological Chemistry, 2003, 1910-1914, vol. 278, No. 3.
Murphy, Craig A., Journal of Experimental Medicine, Dec. 15, 2003, 1951-1957, vol. 198, No. 12.
Cua, Daniel, Letters to Nature, Feb. 13, 2003, 744-748, vol. 421, No. 6924.
Elson, Charles O., Gastroenterology, 2007, 2359-2370, vol. 132, No. 7.
Wong, Chun, Clinical Immunology, 2008, 385-393, vol. 127, No. 3.
Yu, Raymond Y., The Journal of Immunology, 2010, 7302-7308, vol. 185, No. 12.
Murphy, Kenneth, Nature Review Immunology, Dec. 2002, 933-944, vol. 2.
Harrington, LE, Nature Immunology, Nov 2005, 1123-1132, vol. 6, No. 2, Nature Publishing Group.
Langrish, Claire L., The Journal of Experimental Medicine, Jan. 17, 2005, 233-240, vol. 201, No. 2, Rockefeller Univeristy Press.
Harrington, Laurie E., Current Opinion in Immunology, 2006, 349-356, vol. 18.
Korn, Thomas, Seminars in Immunology, 2007, 362-371, vol. 19.
Ouyang, W., Immunity Review, 2008, 454-467, vol. 28, No. 4.
Louten, Jennifer, J Allergy Clin Immunology, 2009, 1004-1011, vol. 123, No. 5.
Abraham, C., Inflammatory Bowel Diseases, 2009, 1090-1100, vol. 15, No. 7.
Zhang, J.H., Biology of Reproduction, 2003, 404-411, vol. 69, No. 2.
Uz, Yesim, Journal of Reproductibe Immunology, 2010, 21-27, vol. 87, No. 1-2.
Nakashima, A., American Journal of Reproductive Immunology, Feb. 2010, 104-109, vol. 63, Issue 2.
Wang, WJ, Journal of Reproductive Immunology, 2010, 164-170, vol. 84, No. 2.
Nakashima, A., American Journal of Reproductive Immunology, Jul. 2010, 4-11, vol. 64, Issue 1.
Bansal, AS, American Journal of Reproductive Immunology, Nov. 2010, 307-315, vol. 64, Issue 5.
Saito, Shigeru, American Journal of Reproductive Immunology, 601-610, vol. 63, No. 5.
Cardoso, CR, Oral Microbiology and Immunology, Feb. 2009, 1-6, vol. 24, Issue 1.
Duerr, RH, Science, Dec. 1, 2006, 1461-1463, vol. 314, No. 5804.
Cargill, M., American Journal of Human Genetics, Feb. 2007, 273-290, vol. 80, No. 2.

* cited by examiner

*Primary Examiner* — Dong Jiang
(74) *Attorney, Agent, or Firm* — Siu K. Lo

(57) ABSTRACT

A naturally-occurring soluble truncated IL-23Rα protein (i.e., Δ9 IL-23Rα) is shown to be present in a biological sample and can serve as a diagnostic tool for autoimmune diseases. There is provided an enzyme-linked immunosorbent assay (ELISA) and test kit for the serological detection of the soluble truncated form of IL-23Rα protein. More particularly, antibody-sandwich ELISA method and kits for Δ9 IL-23Rα as an antigen were developed to detect Δ9 IL-23Rα levels in biological samples from a mammal and a human patient and are used as a diagnostic index. The present disclosed ELISA has utility as a diagnostic tool to detect Crohn's disease in patients using EDTA-plasma.

12 Claims, 35 Drawing Sheets

Figure 32

>Nucleotide (SEQ ID NO: 1)
ATGAATCAGGTCACTATTCAATGGGATGCAGTAATAGCCCTTTACATACTCTTCA
GCTGGTGTCATGGAGGAATTACAAATATAAACTGCTCTGGCCACATCTGGGTAGA
ACCAGCCACAATTTTTAAGATGGGTATGAATATCTCTATATATTGCCAAGCAGCA
ATTAAGAACTGCCAACCAAGGAAACTTCATTTTTATAAAAATGGCATCAAAGAAA
GATTTCAAATCACAAGGATTAATAAAACAACAGCTCGGCTTTGGTATAAAAACTT
TCTGGAACCACATGCTTCTATGTACTGCACTGCTGAATGTCCCAAACATTTTCAA
GAGACACTGATATGTGGAAAAGACATTTCTTCTGGATATCCGCCAGATATTCCTG
ATGAAGTAACCTGTGTCATTTATGAATATTCAGGCAACATGACTTGCACCTGGAA
TGCTGGGAAGCTCACCTACATAGACACAAAATACGTGGTACATGTGAAGAGTTTA
GAGACAGAAGAAGAGCAACAGTATCTCACCTCAAGCTATATTAACATCTCCACTG
ATTCATTACAAGGTGGCAAGAAGTACTTGGTTTGGGTCCAAGCAGCAAACGCACT
AGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCA
TAATTTATTGGGATAGTCAAACAACAATTGAAAAGGTTTCCTGTGAAATGAGATA
CAAGGCTACAACAAACCAAACTTGGAATGTTAAAGAATTTGACACCAATTTTACA
TATGTGCAACAGTCAGAATTCTACTTGGAGCCAAACATTAAGTACGTATTTCAAG
TGAGATGTCAAGAAACAGGCAAAAGGTACTGGCAGCCTTGGAGTTCACTGTTTTT
TCATAAAACACCTGAAACAGTTCCCCAGGTCACATCAAAAGCATTCCAACATGAC
ACATGGAATTCTGGGCTAACAGTTGCTTCCATCTCTACAGGGCACCTTACTTCTG
GATTAAAAGAAGGATCTTATTGTTAA >Protein
Δ9 (SEQ ID NO: 2)
MNQVTIQWDAVIALYILFSWCHGGITNINCSGHIWVEPATIFKMGMNISIYCQAAI
KNCQPRKLHFYKNGIKERFQITRINKTTARLWYKNFLEPHASMYCTAECPKHFQ
ETLICGKDISSGYPPDIPDEVTCVIYEYSGNMTCTWNAGKLTYIDTKYVVHVKSL
ETEEEQQYLTSSYINISTDSLQGGKKYLVWVQAANALGMEESKQLQIHLDDIVIP
SAAVISRAETINATVPKTIIYWDSQTTIEKVSCEMRYKATTNQTWNVKEFDTNFT
YVQQSEFYLEPNIKYVFQVRCQETGKRYWQPWSSLFFHKTPETVPQVTSKAFQH
DTWNSGLTVASISTGHLTSGLKEGSYC

Figure 33

>Nucleotide (SEQ ID NO: 3)
ATGAATCAGGTCACTATTCAATGGGATGCAGTAATAGCCCTTTACATACTCTTCA
GCTGGTGTCATGGAGGAATTACAAATATAAACTGCTCTGGCCACATCTGGGTAGA
ACCAGCCACAATTTTTAAGATGGGTATGAATATCTCTATATATTGCCAAGCAGCA
ATTAAGAACTGCCAACCAAGGAAACTTCATTTTTATAAAAATGGCATCAAAGAAA
GATTTCAAATCACAAGGATTAATAAAACAACAGCTCGGCTTTGGTATAAAAACTT
TCTGGAACCACATGCTTCTATGTACTGCACTGCTGAATGTCCCAAACATTTTCAA
GAGACACTGATATGTGGAAAGACATTTCTTCTGGATATCCGCCAGATATTCCTG
ATGAAGTAACCTGTGTCATTTATGAATATTCAGGCAACATGACTTGCACCTGGAA
TGCTGGGAAGCTCACCTACATAGACACAAAATACGTGGTACATGTGAAGAGTTTA
GAGACAGAAGAAGAGCAACAGTATCTCACCTCAAGCTATATTAACATCTCCACTG
ATTCATTACAAGGTGGCAAGAAGTACTTGGTTTGGGTCCAAGCAGCAAACGCACT
AGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCA
TAATTTATTGGGATAGTCAAACAACAATTGAAAAGGTTTCCTGTGAAATGAGATA
CAAGGCTACAACAAACCAAACTTGGAATGTTAAAGAATTTGACACCAATTTTACA
TATGTGCAACAGTCAGAATTCTACTTGGAGCCAAACATTAAGTACGTATTTCAAG
TGAGATGTCAAGAAACAGGCAAAAGGTACTGGCAGCCTTGGAGTTCACTGTTTTT
TCATAAAACACCTGAAACAGGATTAAAAGAAGGATCTTATTGTTAA >Protein
Δ8,9 (SEQ ID NO: 4)
MNQVTIQWDAVIALYILFSWCHGGITNINCSGHIWVEPATIFKMGMNISIYCQAAI
KNCQPRKLHFYKNGIKERFQITRINKTTARLWYKNFLEPHASMYCTAECPKHFQ
ETLICGKDISSGYPPDIPDEVTCVIYEYSGNMTCTWNAGKLTYIDTKYVVHVKSL
ETEEEQQYLTSSYINISTDSLQGGKKYLVWVQAANALGMEESKQLQIHLDDIVIP
SAAVISRAETINATVPKTIIYWDSQTTIEKVSCEMRYKATTNQTWNVKEFDTNFT
YVQQSEFYLEPNIKYVFQVRCQETGKRYWQPWSSLFFHKTPETGLKEGSYC

Figure 34

>Nucleotide (SEQ ID NO: 8)
ATGAATCAGGTCACTATTCAATGGGATGCAGTAATAGCCCTTTACATACTCTTCA
GCTGGTGTCATGGAGGAATTACAAATATAAACTGCTCTGGCCACATCTGGGTAGA
ACCAGCCACAATTTTTAAGATGGGTATGAATATCTCTATATATTGCCAAGCAGCA
ATTAAGAACTGCCAACCAAGGAAACTTCATTTTTATAAAAATGGCATCAAAGAAA
GATTTCAAATCACAAGGATTAATAAAACAACAGCTCGGCTTTGGTATAAAAACTT
TCTGGAACCACATGCTTCTATGTACTGCACTGCTGAATGTCCCAAACATTTTCAA
GAGACACTGATATGTGGAAAGACATTTCTTCTGGATATCCGCCAGATATTCCTG
ATGAAGTAACCTGTGTCATTTATGAATATTCAGGAACATGACTTGCACCTGGAA
TGCTGGGAAGCTCACCTACATAGACACAAAATACGTGGTACATGTGAAGAGTTTA
GAGACAGAAGAAGAGCAACAGTATCTCACCTCAAGCTATATTAACATCTCCACTG
ATTCATTACAAGGTGGCAAGAAGTACTTGGTTTGGGTCCAAGCAGCAAACGCACT
AGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCA
TAATTTATTGGGATAGTCAAACAACAATTGAAAAGGTTTCCTGTGAAATGAGATA
CAAGGCTACAACAAACCAAACTTGGAATGTTAAAGAATTTGACACCAATTTTACA
TATGTGCAACAGTCAGAATTCTACTTGGAGCCAAACATTAAGTACGTATTTCAAG
TGAGATGTCAAGAAACAGGCAAAAGGTACTGGCAGCCTTGGAGTTCACTGTTTTT
TCATAAAACACCTGAAACAGTTCCCCAGGTCACATCAAAAGCATTCAACATGAC
ACATGGAATTCTGGGCTAACAGTTGCTTCCATCTCTACAGGGCACCTTACTTCTG
ACAACAGAGGAGACATTGGACTTTTATTGGGAATGATCGTCTTTGCTGTTATGTT
GTCAATTCTTTCTTTGATTGGGATATTTAACAGATCATTCCGAACTGGGATTAAA
AGAAGGATCTTATTGTTAATACCAAAGTGGCTTTATGAAGATATTCCTAATATGA
AAAACAGCAATGTTGTGAAAATGCTACAGAGATAA >Protein
pΔ11 (SEQ ID NO: 9)
MNQVTIQWDAVIALYILFSWCHGGITNINCSGHIWVEPATIFKMGMNISIYCQAAI
KNCQPRKLHFYKNGIKERFQITRINKTTARLWYKNFLEPHASMYCTAECPKHFQ
ETLICGKDISSGYPPDIPDEVTCVIYEYSGNMTCTWNAGKLTYIDTKYVVHVKSL
ETEEEQQYLTSSYINISTDSLQGGKKYLVWVQAANALGMEESKQLQIHLDDIVIP
SAAVISRAETINATVPKTIIYWDSQTTIEKVSCEMRYKATTNQTWNVKEFDTNFT
YVQQSEFYLEPNIKYVFQVRCQETGKRYWQPWSSLFFHKTPETVPQVTSKAFQH
DTWNSGLTVASISTGHLTSDNRGDIGLLLGMIVFAVMLSILSLIGIFNRSFRTGIKR
RILLLIPKWLYEDIPNMKNSNVVKMLQR

Figure 35

>Nucleotide (SEQ ID NO: 10)
ATGAATCAGGTCACTATTCAATGGGATGCAGTAATAGCCCTTTACATACTCTTCAGCTGG
TGTCATGGAGGAATTACAAATATAAACTGCTCTGGCCACATCTGGGTAGAACCAGCCACA
ATTTTTAAGATGGGTATGAATATCTCTATATATTGCCAAGCAGCAATTAAGAACTGCCAA
CCAAGGAAACTTCATTTTTATAAAAATGGCATCAAAGAAAGATTTCAAATCACAAGGATT
AATAAAACAACAGCTCGGCTTTGGTATAAAAACTTTCTGGAACCACATGCTTCTATGTAC
TGCACTGCTGAATGTCCCAAACATTTTCAAGAGACACTGATATGTGGAAAGACATTTCT
TCTGGATATCCGCCAGATATTCCTGATGAAGTAACCTGTGTCATTTATGAATATTCAGGC
AACATGACTTGCACCTGGAATGCTGGGAAGCTCACCTACATAGACACAAAATACGTGGTA
CATGTGAAGAGTTTAGAGACAGAAGAAGAGCAACAGTATCTCACCTCAAGCTATATTAAC
ATCTCCACTGATTCATTACAAGGTGGCAAGAAGTACTTGGTTTGGGTCCAAGCAGCAAAC
GCACTAGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCATAATT
TATTGGGATAGTCAAACAACAATTGAAAAGGTTTCCTGTGAAATGAGATACAAGGCTACA
ACAAACCAAACTTGGAATGTTAAAGAATTTGACACCAATTTTACATATGTGCAACAGTCA
GAATTCTACTTGGAGCCAAACATTAAGTACGTATTTCAAGTGAGATGTCAAGAAACAGGC
AAAAGGTACTGGCAGCCTTGGAGTTCACTGTTTTTTCATAAAACACCTGAAACAGACAAC
AGAGGAGACATTGGACTTTTATTGGGAATGATCGTCTTTGCTGTTATGTTGTCAATTCTT
TCTTTGATTGGGATATTTAACAGATCATTCCGAACTGGGATTAAAAGAAGGATCTTATTG
TTAATACCAAAGTGGCTTTATGAAGATATTCCTAATATGAAAAACAGCAATGTTGTGAAA
ATGCTACAGGAAAATAGTGAACTTATGAATAATAATTCCAGTGAGCAGGTCCTATATGTT
GATCCCATGATTACAGAGATAAAAGAAATCTTCATCCCAGAACACAAGCCTACAGACTAC
AAGAAGGAGAATACAGGACCCCTGGAGACAAGAGACTACCCGCAAAACTCGCTATTCGAC
AATACTACAGTTGTATATATTCCTGATCTCAACACTGGATATAAACCCCAAATTTCAAAT
TTTCTGCCTGAGGGAAGCCATCTCAGCAATAATAATGAAATTACTTCCTTAACACTTAAA
CCACCAGTTGATTCCTTAGACTCAGGAAATAATCCCAGGTTACAAAAGCATCCTAATTTT
GCTTTTTCTGTTTCAAGTGTGAATTCACTAAGCAACACAATATTTCTTGGAGAATTAAGC
CTCATATTAAATCAAGGAGAATGCAGTTCTCCTGACATACAAAACTCAGTAGAGGAGGAA
ACCACCATGCTTTTGGAAAATGATTCACCCAGTGAAACTATTCCAGAACAGACCCTGCTT
CCTGATGAATTTGTCTCCTGTTTGGGGATCGTGAATGAGGAGTTGCCATCTATTAATACT
TATTTTCCACAAAATATTTTGGAAAGCCACTTCAATAGGATTTCACTCTTGGAAAAGTAG >Protein
Δ8 (SEQ ID NO: 11)
MNQVTIQWDAVIALYILFSWCHGGITNINCSGHIWVEPATIFKMGMNISIYCQAAIKNCQ
PRKLHFYKNGIKERFQITRINKTTARLWYKNFLEPHASMYCTAECPKHFQETLICGKDIS
SGYPPDIPDEVTCVIYEYSGNMTCTWNAGKLTYIDTKYVVHVKSLETEEEQQYLTSSYIN
ISTDSLQGGKKYLVWVQAANALGMEESKQLQIHLDDIVIPSAAVISRAETINATVPKTII
YWDSQTTIEKVSCEMRYKATTNQTWNVKEFDTNFTYVQQSEFYLEPNIKYVFQVRCQETG
KRYWQPWSSLFFHKTPETDNRGDIGLLLGMIVFAVMLSILSLIGIFNRSFRTGIKRRILL
LIPKWLYEDIPNMKNSNVVKMLQENSELMNNNSSEQVLYVDPMITEIKEIFIPEHKPTDY
KKENTGPLETRDYPQNSLFDNTTVVYIPDLNTGYKPQISNFLPEGSHLSNNNEITSLTLK
PPVDSLDSGNNPRLQKHPNFAFSVSSVNSLSNTIFLGELSLILNQGECSSPDIQNSVEEE
TTMLLENDSPSETIPEQTLLPDEFVSCLGIVNEELPSINTYFPQNILESHFNRISLLEK

SEQUENCE LISTING

```
<160> NUMBER OF SEQ ID NOS: 23

<210> SEQ ID NO 1
<211> LENGTH: 1071
<212> TYPE: DNA
<213> ORGANISM: Homo sapiens

<400> SEQUENCE: 1
atgaatcagg tcactattca atgggatgca gtaatagccc tttacatact cttcagctgg      60
tgtcatggag gaattacaaa tataaactgc tctggccaca tctgggtaga accagccaca     120 attttttaaga tgggtatgaa tatctctata tattgccaag cagcaattaa gaactgccaa     180
ccaaggaaac ttcattttta taaaatggc atcaagaaa gatttcaaat cacaaggatt      240
aataaaacaa cagctcggct ttggtataaa aactttctgg aaccacatgc ttctatgtac     300
tgcactgctg aatgtcccaa acattttcaa gagacactga tatgtggaaa agacatttct     360
tctggatatc cgccagatat tcctgatgaa gtaacctgtg tcatttatga atattcaggc     420
aacatgactt gcacctggaa tgctgggaag ctcacctaca tagacacaaa atacgtggta     480
catgtgaaga gtttagagac agaagaagag caacagtatc tcacctcaag ctatattaac     540
atctccactg attcattaca aggtggcaag aagtacttgg tttgggtcca agcagcaaac     600
gcactaggca tggaagagtc aaaacaactg caaattcacc tggatgatat agtgatacct     660
tctgcagccg tcatttccag ggctgagact ataaatgcta cagtgccaa gaccataatt     720 tattgggata gtcaaacaac aattgaaaag gtttcctgtg aaatgagata caaggctaca     780
```

```
acaaaccaaa cttggaatgt taaagaattt gacaccaatt ttacatatgt gcaacagtca    840
gaattctact tggagccaaa cattaagtac gtatttcaag tgagatgtca agaaacaggc    900
aaaaggtact ggcagccttg gagttcactg ttttttcata aaacacctga aacagttccc    960
caggtcacat caaaagcatt ccaacatgac acatggaatt ctgggctaac agttgcttcc   1020
atctctacag ggcaccttac ttctggatta aagaaggat cttattgtta a            1071
```

<210> SEQ ID NO 2
<211> LENGTH: 356
<212> TYPE: PRT
<213> ORGANISM: Homo sapiens

<400> SEQUENCE: 2

```
Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320
```

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Gly Leu Lys Glu
            340                 345                 350

Gly Ser Tyr Cys
        355

<210> SEQ ID NO 3
<211> LENGTH: 981
<212> TYPE: DNA
<213> ORGANISM: Homo sapiens

<400> SEQUENCE: 3

```
atgaatcagg tcactattca atgggatgca gtaatagccc tttacatact cttcagctgg      60
tgtcatggag gaattacaaa tataaactgc tctggccaca tctgggtaga accagccaca     120
attttaaga tgggtatgaa tatctctata tattgccaag cagcaattaa gaactgccaa     180
ccaaggaaac ttcattttta taaaaatggc atcaaagaaa gatttcaaat cacaaggatt     240
aataaaacaa cagctcggct tggtataaaa actttctgg aaccacatgc ttctatgtac     300
tgcactgctg aatgtcccaa acattttcaa gagacactga tatgtggaaa agacatttct     360
tctggatatc cgccagatat tcctgatgaa gtaacctgtg tcatttatga atattcaggc     420
aacatgactt gcacctggaa tgctgggaag ctcacctaca tagacacaaa atacgtggta     480
catgtgaaga gtttagagac agaagaagag caacagtatc tcacctcaag ctatattaac     540
atctccactg attcattaca aggtggcaag aagtacttgg tttgggtcca agcagcaaac     600
gcactaggca tggaagagtc aaaacaactg caaattcacc tggatgatat agtgatacct     660
tctgcagccg tcatttccag ggctgagact ataaatgcta cagtgcccaa gaccataatt     720
tattgggata gtcaaacaac aattgaaaag gtttcctgtg aaatgagata caaggctaca     780
acaaaccaaa cttggaatgt taagaatttt gacaccaatt ttacatatgt gcaacagtca     840
gaattctact ggagccaaaa cattaagtac gtatttcaag tgagatgtca agaaacaggc     900
aaaaggtact ggcagccttg gagttcactg ttttttcata aaacacctga aacaggatta     960
aaagaaggat cttattgtta a                                              981
```

<210> SEQ ID NO 4
<211> LENGTH: 326
<212> TYPE: PRT
<213> ORGANISM: Homo sapiens

<400> SEQUENCE: 4

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

-continued

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
            165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
            245                 250                 255

Tyr Lys Ala Thr Thr Asn Gln Thr Trp Asn Val Lys Glu Phe Asp Thr
        260                 265                 270

Asn Phe Thr Tyr Val Gln Gln Ser Glu Phe Tyr Leu Glu Pro Asn Ile
    275                 280                 285

Lys Tyr Val Phe Gln Val Arg Cys Gln Glu Thr Gly Lys Arg Tyr Trp
290                 295                 300

Gln Pro Trp Ser Ser Leu Phe Phe His Lys Thr Pro Glu Thr Gly Leu
305                 310                 315                 320

Lys Glu Gly Ser Tyr Cys
                325

<210> SEQ ID NO 5
<211> LENGTH: 24
<212> TYPE: DNA
<213> ORGANISM: Homo sapiens

<400> SEQUENCE: 5
caggttgaaa gagggaaaca gtct                                              24

<210> SEQ ID NO 6
<211> LENGTH: 58
<212> TYPE: DNA
<213> ORGANISM: Homo sapiens

<400> SEQUENCE: 6
ctcgagctac ttgtcatcgt cgtccttgta atcctttcc aagagtgaaa tcctaatg         58

<210> SEQ ID NO 7
<211> LENGTH: 8
<212> TYPE: PRT
<213> ORGANISM: Homo sapiens

<400> SEQUENCE: 7

Gly Leu Lys Glu Gly Ser Tyr Cys
1               5

<210> SEQ ID NO 8
<211> LENGTH: 1245
<212> TYPE: DNA
<213> ORGANISM: Homo sapiens

<400> SEQUENCE: 8

```
atgaatcagg tcactattca atgggatgca gtaatagccc tttacatact cttcagctgg      60
tgtcatggag gaattacaaa tataaactgc tctggccaca tctgggtaga accagccaca     120
attttaaga tgggtatgaa tatctctata tattgccaag cagcaattaa gaactgccaa      180
ccaaggaaac ttcatttta taaaaatggc atcaagaaa gatttcaaat cacaaggatt      240
aataaaacaa cagctcggct ttggtataaa aactttctgg aaccacatgc ttctatgtac     300
tgcactgctg aatgtcccaa acattttcaa gagacactga tatgtggaaa agacatttct     360
tctggatatc cgccagatat tcctgatgaa gtaacctgtg tcatttatga atattcaggc     420
aacatgactt gcacctggaa tgctgggaag ctcacctaca tagacacaaa atacgtggta     480
catgtgaaga gtttagagac agaagaagag caacagtatc tcacctcaag ctatattaac     540
atctccactg attcattaca aggtggcaag aagtacttgg tttgggtcca agcagcaaac     600
gcactaggca tggaagagtc aaaacaactg caaattcacc tggatgatat agtgatacct     660
tctgcagccg tcatttccag ggctgagact ataaatgcta cagtgcccaa gaccataatt     720
tattgggata gtcaaacaac aattgaaaag gtttcctgtg aaatgagata caaggctaca     780
acaaaccaaa cttggaatgt taagaatttt gacaccaatt ttacatatgt gcaacagtca     840
gaattctact ggagccaaa cattaagtac gtatttcaag tgagatgtca agaaacaggc     900
aaaaggtact ggcagccttg gagttcactg ttttttcata aacacctga acagttccc      960
caggtcacat caaaagcatt ccaacatgac acatggaatt ctgggctaac agttgcttcc    1020
atctctacag ggcaccttac ttctgacaac agaggagaca ttggactttt attgggaatg    1080
atcgtctttg ctgttatgtt gtcaattctt tctttgattg ggatatttaa cagatcattc    1140
cgaactggga ttaaaagaag gatcttattg ttaataccaa agtggcttta tgaagatatt    1200
cctaatatga aaacagcaa tgttgtgaaa atgctacaga gataa                    1245
```

<210> SEQ ID NO 9
<211> LENGTH: 414
<212> TYPE: PRT
<213> ORGANISM: Homo sapiens

<400> SEQUENCE: 9

```
Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140
```

```
Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
            165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
            195                 200                 205

Gln Leu Gln Ile His Leu Asp Asp Ile Val Ile Pro Ser Ala Ala Val
210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
            245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
            275                 280                 285

Lys Tyr Val Phe Gln Val Arg Cys Gln Glu Thr Gly Lys Arg Tyr Trp
            290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
            325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
            355                 360                 365

Ile Leu Ser Leu Ile Gly Ile Phe Asn Arg Ser Phe Arg Thr Gly Ile
370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Arg
            405                 410

<210> SEQ ID NO 10
<211> LENGTH: 1800
<212> TYPE: DNA
<213> ORGANISM: Homo sapiens

<400> SEQUENCE: 10
atgaatcagg tcactattca atgggatgca gtaatagccc tttacatact cttcagctgg    60
tgtcatggag gaattacaaa tataaactgc tctggccaca tctgggtaga accagccaca   120 attttaaga tgggtatgaa tatctctata tattgccaag cagcaattaa gaactgccaa   180
ccaaggaaac ttcattttta taaaaatggc atcaaagaaa gatttcaaat cacaaggatt   240
aataaaacaa cagctcggct ttggtataaa aactttctgg aaccacatgc ttctatgtac   300
tgcactgctg aatgtcccaa acattttcaa gagacactga tatgtggaaa agacatttct   360
tctggatatc cgccagatat tcctgatgaa gtaacctgtg tcatttatga atattcaggc   420
aacatgactt gcacctggaa tgctgggaag ctcacctaca tagacacaaa atacgtggta   480
catgtgaaga gtttagagac agaagaagag caacagtatc tcacctcaag ctatattaac   540
atctccactg attcattaca aggtggcaag aagtacttgg tttgggtcca agcagcaaac   600
```

```
gcactaggca tggaagagtc aaaacaactg caaattcacc tggatgatat agtgatacct    660
tctgcagccg tcatttccag ggctgagact ataaatgcta cagtgcccaa gaccataatt    720
tattgggata gtcaaacaac aattgaaaag gtttcctgtg aaatgagata caaggctaca    780
acaaaccaaa cttggaatgt taaagaattt gacaccaatt ttacatatgt gcaacagtca    840
gaattctact tggagccaaa cattaagtac gtattttcaag tgagatgtca agaaacaggc    900
aaaaggtact ggcagccttg gagttcactg ttttttcata aaacacctga acagacaac     960 agaggagaca ttggactttt attgggaatg atcgtctttg ctgttatgtt gtcaattctt   1020
tctttgattg ggatatttaa cagatcattc cgaactggga ttaaaagaag gatcttattg   1080
ttaataccaa gtggctttta tgaagatatt cctaatatga aaaacagcaa tgttgtgaaa   1140
atgctacagg aaaatagtga acttatgaat aataattcca gtgagcaggt cctatatgtt   1200
gatcccatga ttacagagat aaaagaaatc ttcatcccag aacacaagcc tacagactac   1260
aagaaggaga atacaggacc cctggagaca agagactacc cgcaaaactc gctattcgac   1320
aatactacag ttgtatatat tcctgatctc aacactggat ataaacccca aatttcaaat   1380
tttctgcctg agggaagcca tctcagcaat aataatgaaa ttacttcctt aacacttaaa   1440
ccaccagttg attccttaga ctcaggaaat aatcccaggt tacaaaagca tcctaatttt   1500 gcttttctg tttcaagtgt gaattcacta agcaacacaa tatttcttgg agaattaagc    1560
ctcatattaa atcaaggaga atgcagttct cctgacatac aaaactcagt agaggaggaa   1620
accaccatgc ttttggaaaa tgattcaccc agtgaaacta ttccagaaca gaccctgctt   1680
cctgatgaat ttgtctcctg tttggggatc gtgaatgagg agttgccatc tattaatact   1740
tattttccac aaaatatttt ggaaagccac ttcaatagga tttcactctt ggaaaagtag   1800
```

<210> SEQ ID NO 11
<211> LENGTH: 599
<212> TYPE: PRT
<213> ORGANISM: Homo sapiens

<400> SEQUENCE: 11

```
Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160
```

```
His Val Lys Ser Leu Glu Thr Glu Glu Gln Gln Tyr Leu Thr Ser
            165                 170                 175

Ser Tyr Ile Asn Ile Ser Thr Asp Ser Leu Gln Gly Lys Lys Tyr
            180                 185                 190

Leu Val Trp Val Gln Ala Ala Asn Ala Leu Gly Met Glu Glu Ser Lys
            195                 200                 205

Gln Leu Gln Ile His Leu Asp Asp Ile Val Ile Pro Ser Ala Ala Val
            210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
            245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
            275                 280                 285

Lys Tyr Val Phe Gln Val Arg Cys Gln Glu Thr Gly Lys Arg Tyr Trp
            290                 295                 300

Gln Pro Trp Ser Ser Leu Phe Phe His Lys Thr Pro Glu Thr Asp Asn
305                 310                 315                 320

Arg Gly Asp Ile Gly Leu Leu Leu Gly Met Ile Val Phe Ala Val Met
            325                 330                 335

Leu Ser Ile Leu Ser Leu Ile Gly Ile Phe Asn Arg Ser Phe Arg Thr
            340                 345                 350

Gly Ile Lys Arg Arg Ile Leu Leu Leu Ile Pro Lys Trp Leu Tyr Glu
            355                 360                 365

Asp Ile Pro Asn Met Lys Asn Ser Asn Val Val Lys Met Leu Gln Glu
            370                 375                 380

Asn Ser Glu Leu Met Asn Asn Asn Ser Ser Glu Gln Val Leu Tyr Val
385                 390                 395                 400

Asp Pro Met Ile Thr Glu Ile Lys Glu Ile Phe Ile Pro Glu His Lys
            405                 410                 415

Pro Thr Asp Tyr Lys Lys Glu Asn Thr Gly Pro Leu Glu Thr Arg Asp
            420                 425                 430

Tyr Pro Gln Asn Ser Leu Phe Asp Asn Thr Thr Val Val Tyr Ile Pro
            435                 440                 445

Asp Leu Asn Thr Gly Tyr Lys Pro Gln Ile Ser Asn Phe Leu Pro Glu
            450                 455                 460

Gly Ser His Leu Ser Asn Asn Asn Glu Ile Thr Ser Leu Thr Leu Lys
465                 470                 475                 480

Pro Pro Val Asp Ser Leu Asp Ser Gly Asn Asn Pro Arg Leu Gln Lys
            485                 490                 495

His Pro Asn Phe Ala Phe Ser Val Ser Ser Val Asn Ser Leu Ser Asn
            500                 505                 510

Thr Ile Phe Leu Gly Glu Leu Ser Leu Ile Leu Asn Gln Gly Glu Cys
            515                 520                 525

Ser Ser Pro Asp Ile Gln Asn Ser Val Glu Glu Thr Thr Met Leu
            530                 535                 540

Leu Glu Asn Asp Ser Pro Ser Glu Thr Ile Pro Glu Gln Thr Leu Leu
545                 550                 555                 560

Pro Asp Glu Phe Val Ser Cys Leu Gly Ile Val Asn Glu Glu Leu Pro
            565                 570                 575

Ser Ile Asn Thr Tyr Phe Pro Gln Asn Ile Leu Glu Ser His Phe Asn
```

Arg Ile Ser Leu Leu Glu Lys
    595

<210> SEQ ID NO 12
<211> LENGTH: 22
<212> TYPE: DNA
<213> ORGANISM: Homo sapiens

<400> SEQUENCE: 12
atgaatcagg tcacattcaa tg                                              22

<210> SEQ ID NO 13
<211> LENGTH: 52
<212> TYPE: DNA
<213> ORGANISM: Homo sapiens

<400> SEQUENCE: 13
ctacttgtca tcgtcgtcct tgtaatcctt ttccaagagt gaaatcctat tg             52

<210> SEQ ID NO 14
<211> LENGTH: 22
<212> TYPE: DNA
<213> ORGANISM: Homo sapiens

<400> SEQUENCE: 14
atgaatcagg tcacattcaa tg                                              22

<210> SEQ ID NO 15
<211> LENGTH: 54
<212> TYPE: DNA
<213> ORGANISM: Homo sapiens

<400> SEQUENCE: 15
ctacttgtca tcgtcgtcct tgtaatctct ctgtagcatt ttcacaacat tgct           54

<210> SEQ ID NO 16
<211> LENGTH: 22
<212> TYPE: DNA
<213> ORGANISM: Homo sapiens

<400> SEQUENCE: 16
atgaatcagg tcacattcaa tg                                              22

<210> SEQ ID NO 17
<211> LENGTH: 64
<212> TYPE: DNA
<213> ORGANISM: Homo sapiens

<400> SEQUENCE: 17
ctacttgtca tcgtcgtcct tgtaatcaca ataagatcct tcttttaatc cagaagtaag     60
gtgc                                                                  64

<210> SEQ ID NO 18
<211> LENGTH: 22
<212> TYPE: DNA
<213> ORGANISM: Homo sapiens

<400> SEQUENCE: 18
atgaatcagg tcacattcaa tg                                              22

<210> SEQ ID NO 19

```
<211> LENGTH: 64
<212> TYPE: DNA
<213> ORGANISM: Homo sapiens

<400> SEQUENCE: 19
ctacttgtca tcgtcgtcct tgtaatcaca ataagatcct tcttttaatc ctgtttcagg    60
tgtt                                                                 64

<210> SEQ ID NO 20
<211> LENGTH: 22
<212> TYPE: DNA
<213> ORGANISM: Homo sapiens

<400> SEQUENCE: 20
atgaatcagg tcacattcaa tg                                             22

<210> SEQ ID NO 21
<211> LENGTH: 14
<212> TYPE: DNA
<213> ORGANISM: Homo sapiens

<400> SEQUENCE: 21
ctgtttcagg tgtt                                                      14

<210> SEQ ID NO 22
<211> LENGTH: 14
<212> TYPE: DNA
<213> ORGANISM: Homo sapiens

<400> SEQUENCE: 22
aacacctgaa acag                                                      14

<210> SEQ ID NO 23
<211> LENGTH: 52
<212> TYPE: DNA
<213> ORGANISM: Homo sapiens

<400> SEQUENCE: 23
ctacttgtca tcgtcgtcct tgtaatcctt ttccaagagt gaaatcctat tg            52
```

ELISA FOR A NATURALLY-OCCURRING SOLUBLE TRUNCATED FORM OF IL-23 RECEPTOR

CROSS-REFERENCE TO RELATED APPLICATIONS

This application claims the benefit under 35 U.S.C. §119 (e) to U.S. Provisional Application Nos. 61/341,457, 61/341,465 filed Mar. 31, 2010, the contents of which are incorporated by reference herein in their entireties.

FIELD OF THE INVENTION

The present invention relates generally to an immunoassay for detecting a naturally-occurring soluble truncated form of IL-23 receptor (IL-23Rα). More specifically, the present invention provides an ELISA assay for a soluble truncated form (e.g., Δ9 protein) of IL-23Rα. The assay is useful as a diagnostic tool in patients afflicted with immunological diseases including inflammatory bowel diseases (e.g., Crohn's disease), asthma, and other pathological diseases such as miscarriage.

BACKGROUND OF THE INVENTION

IL-23 is a heterodimeric molecule comprising a p19 subunit and a p40 subunit that are two disulfide-linked. IL-23 is speculated to play an essential role in chronic inflammation and autoimmune diseases in humans. Mice lacking p19 exhibit a decreased pro-inflammatory response to experimental autoimmune encephalomyelitis, inflammatory bowel disease and collagen-induced arthritis. While IL-23 per se cannot induce the differentiation of naïve CD4 T-cells into Th-17 cells in vitro, the differentiation of Th17 cells in vivo may require IL-23. The observed protective effect in p19-deficient mice may relate to the lack of differentiation of Th17 cells. This is consistent with recent report that IL-23 synergies with Th17 cell differentiation cytokines including IL-1, IL-6 and TGF-β to induce expression of IL-17.

IL-23 exerts its biological activities by binding to IL-23 receptor (IL-23R). IL-23R comprises an IL-23Rα subunit and an IL-12Rβ1 subunit. When IL-23 binds to IL-23R, it leads to intracellular signaling including phosphorylation of STAT1, STAT3, STAT4 and STAT5. IL-23R is expressed on T-cells, NK cells, monocytes, and dendritic cells and its expression pattern corresponds with the ability of these cells to respond to IL-23.

Human IL-23Rα mRNA is 2.8 kb long and contains 11 exons (NM_144701). The translated full-length IL-23Rα protein is a type-I transmembrane protein (629 amino acids) and contains at least three (3) known structural domains: (1) a signal peptide domain; (2) an extracellular region containing a N-terminal fibronectin III-like domain; and (3) a 253 amino acid residue cytoplasmic domain with three (3) potential tyrosine phosphorylation sites.

Christi Parham et al. first discovered the genomic and structural organization of the IL-23R (composed of an IL-23α subunit and an IL-12Rβ1 subunit). While IL-23 is shown to bind to IL-23R and mediates Jak-STAT cell signaling, Parham explicitly stated their inability to demonstrate human IL-23R-Ig and soluble human IL-23Rα-V5-His6 (composed of the entire extracellular domain—amino acids 1-353) as effective antagonists for human IL-23R. Daniel J. Cua et al. disclose treatment methods for multiple sclerosis, neuropathic pain, and inflammatory bowel disorders using antibodies against IL-23 and its receptor. Contrary to Parham's statement, Cua proposes using a soluble receptor based on the extracellular region of a subunit of the IL-23 receptor (PCT/US2004/003126) as an antagonist. A recombinant human IL-23Rα Fc chimeric protein is commercially available (R&D Systems) and claimed to have the ability to inhibit IL-23 induced IL-17 secretion in a mouse splenocytes system. It remains unclear as to whether any of these proposed soluble IL-23Rαs may in fact exist in vivo as a naturally-occurring protein, let alone the possibility that such soluble IL-23Rs may possess ability to block IL-23Rα mediated cell signaling. To this end, Daniel J. Cua et al. (PCT/US2004/003126) failed to provide any evidence that a soluble IL-23 receptor can indeed block IL-23 mediated cell signaling as well as inhibiting Th17 producing cells.

Recent evidence suggests that IL-23Rα gene may undergo extensive alternative splicing. There are at least twenty-four (24) potential gene transcripts for IL-23Rα. From these IL-23Rα alternatively spliced mRNA sequences, there appears at least four (4) deduced putative translated proteins: (1) a short premature IL-23Rα extracellular peptide; (2) a possible soluble form of IL-23Rα lacking a transmembrane/intracellular domain; (3) a full-length IL-23Rα with truncated extracellular region; and (4) a non-responsive membrane-bound receptor isoform of IL-23Rα with deletion in intracellular signaling components.

Although many gene transcripts for IL-23 Rα (i.e., IL-23R splice variants) are suggested, it is important to point out that their actual existence in vivo is presently unknown. There is little information regarding whether any of the deduced IL-23Rα translated products actually exist in vivo, let alone the function of these IL-23Rα protein variants, if any.

Accordingly, there is a continuing need for a diagnostic assay that detects a measurable level of IL-23Rα variants in a biological sample in a mammal, specifically an accurate ELISA that measures an isoform of IL-23Rα. The assay would enable the assessment of a pathological role of IL-23Rα using biological samples obtained from patients. The present inventors overcome the prior art deficiency and discovered an ELISA assay for quantifying a naturally-occurring soluble truncated form of IL-23Rα (i.e., Δ9 IL-23Rα) in plasma. The present ELISA reveals that a particular form (i.e., Δ9 IL-23Rα) of IL-23Rα constitutes a major spliced variant form of IL-23Rα in plasma and that its level correlates with inflammatory bowel diseases such as Crohn's disease.

SUMMARY OF THE INVENTION

In one aspect, the present invention provides a method for detecting a Δ9 isoform of IL-23 receptor (IL-23Rα) in a biological sample, comprising the steps of: a) obtaining a biological sample; b) incubating said biological sample with a capture reagent immobilized on a solid support to bind a Δ9 isoform of IL-23Rα, wherein the capture reagent comprises a first antibody; and (c) detecting IL-23Rα bound to said immobilized capture reagent by contacting the bound IL-23Rα with a second antibody against IL-23Rα, coupled with a detecting agent. Preferably, the first antibody recognizes or binds to the carboxyl-terminus (C-terminus) of IL-23Rα. More preferably, the first antibody recognizes the exon 8 of the IL-23Rα (i.e., at a site between amino acids 318-348). It is intended that the present invention also cover the first antibody that may equivalently recognize the proximity of amino acids 318-348 and still function as capture antibody. Such an antibody would be specific for detecting Δ9.

The second antibody preferably recognizes the extracellular domain of the IL-23Rα, so as to provide detection for Δ9. Preferably, the first antibody recognizes an epitope that is distinct (i.e., does not overlap) with that of the second antibody.

The first antibody may be a monoclonal antibody or a polyclonal antibody. Preferably, the first antibody is a monoclonal antibody. The second antibody may also be a monoclonal antibody or a polyclonal antibody. Preferably, the second antibody is a polyclonal antibody.

Preferably, the biological sample is selected from the group consisting of blood and plasma. Preferably, the biological sample comprising EDTA. More preferably, the biological sample is EDTA-treated plasma.

Preferably, the incubating step is performed at a pH is about 6.0 to about 10.0. More preferably, the incubating step is performed at pH is about 9.5.

Preferably, the incubating step is performed at a temperature of about 0° C. to about 25° C. More preferably, the incubating step is performed at a temperature of about 4° C.

Preferably, the incubating step is performed for about 0.5 to about 16 hours. More preferably, the incubating step is performed for about 3 hours.

In another aspect, the present invention provides a kit for detecting Δ9 isoform of IL-23Rα, comprising: a) a first antibody that binds to carboxyl-terminal truncated Δ9 isoform of IL-23Rα, wherein the carboxyl-terminal truncated Δ9 isoform of IL-23R comprises amino acids 318-348 of IL-23Rα; and; b) instructions for using the antibody for detecting Δ9 isoform of IL-23Rα.

Preferably, said first antibody is immobilized to a solid support. Preferably, the kit further comprises a second antibody that specifically binds to extracellular domain of IL-23Rα.

Preferably, said first antibody is a monoclonal antibody and said second antibody is a polyclonal antibody.

Preferably, said instructions provide guidance to the use of the kit to detect Δ9 isoform of IL-23Rα in a biological sample.

Preferably, the kit detects Δ9 isoform of IL-23Rα in plasma.

DESCRIPTION OF THE DRAWINGS

FIG. 16 depicts that a IL-23Rα protein is secreted. The developed ELISA detects the purified Δ9 recombinant IL-23Rα.

FIG. 32 depicts the nucleotide sequence of Δ9 (SEQ ID NO: 1) and amino acid sequence of Δ9 (SEQ ID NO: 2).

FIG. 33 depicts the nucleotide sequence of Δ8,9 (SEQ ID NO: 3) and amino acid sequence of Δ8,9 (SEQ ID NO: 4).

FIG. 34 depicts the nucleotide sequence of pΔ11 (SEQ ID NO: 8) and amino acid sequence of pΔ11 (SEQ ID NO: 9).

FIG. 35 depicts the nucleotide sequence of Δ8 (SEQ ID NO: 10) and amino acid sequence of Δ8 (SEQ ID NO: 11).

DETAILED DESCRIPTION OF THE PREFERRED EMBODIMENTS

Definitions

Figure 1:
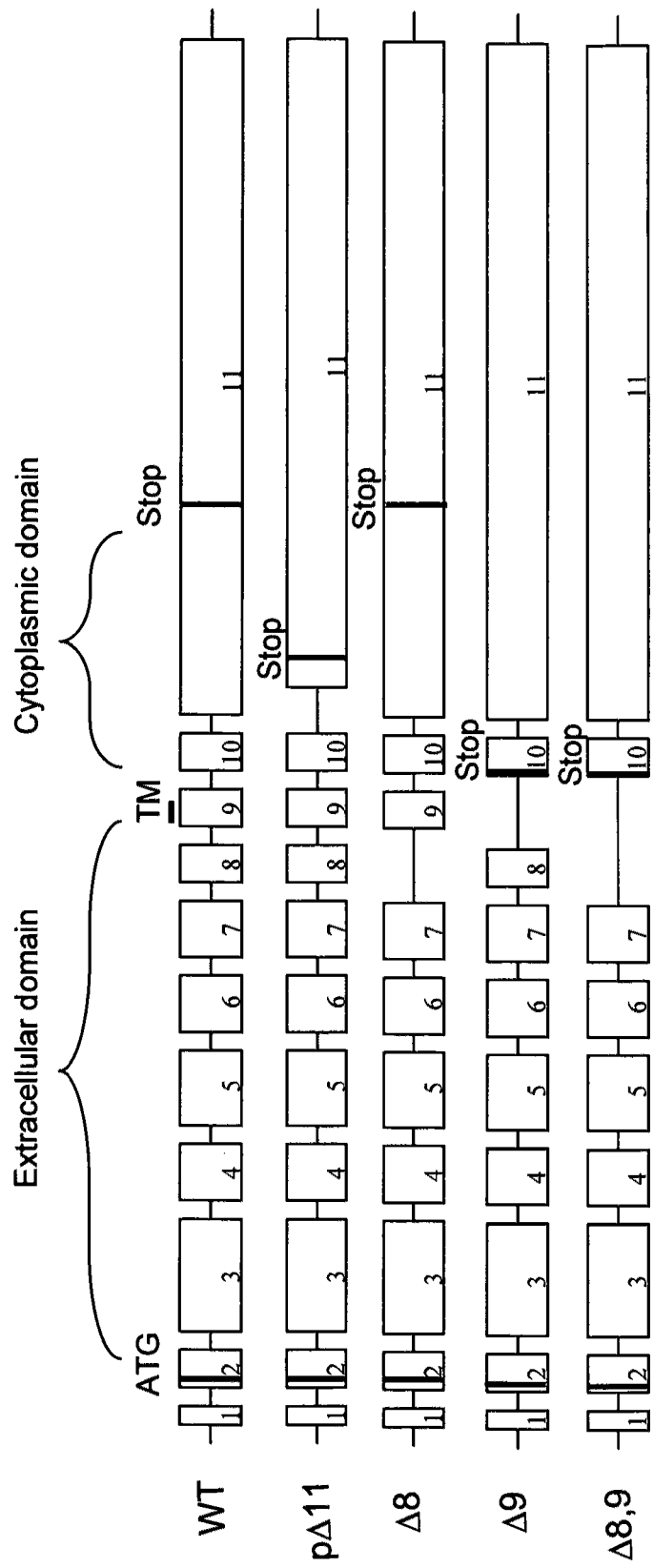
FIG. 1 depicts schematically the constructs of wild-type IL-23Rα and IL-23Rα variants. Partial deletion of exon 11 (pΔ11), deletion of exon 9 (Δ9) and deletion of exon 8 and 9 (Δ8,9) resulted in open reading frame shift, which generated pre-mature translational termination signal. However, deletion of exon 8 (Δ8) was in-frame deletion. Therefore, Δ8 variant used the same translation termination signal at Exon 11 as wild-type IL-23Rα. These expression constructs were constructed by PCR amplification and cloned into pcDNA3.3 expression vector using TOPO cloning kit from Invitrogen. All the constructs were sequence verified.

As used herein, the term "IL-23R" refers to interleukin-23 receptor. IL-23R is composed of two (2) subunits: IL-23Rα and IL-12Rβ1. The IL-23Rα gene is located on chromosome 1p31.3. The native form of human IL-23Rα mRNA is 2.8 kb long and contains 11 exons (NM_144701). The transcribed mRNA is translated into a full-length protein of 629 amino acids, the sequence of which is listed in NM_144701. The full-length translated IL-23Rα protein is a type I cytokine receptor and forms with human IL-12Rβ1 to form the heterodimeric IL-23 receptor. Human IL-12Rβ1 also partners with human IL-12Rβ2 to form the cell-surface IL-12 receptor. When bound to IL-23, this protein triggers a series of cell signaling event including activation of Janus kinase 2 (JAK2), and transcription activator STAT3 (i.e., IL-23R mediated cell signaling). IL-23R is present on many immune system cells, including T cells, natural killer (NK) cells, monocytes, and dendritic cells.

As used herein, for purposes of this application, the term "Δ9" refers to the naturally-occurring truncated IL-23Rα protein resulting from IL-23R mRNA splicing. For purposes of this application, "Δ9 variant", "Δ9 isoform", and "Δ9 protein" are used interchangeably to refer to this particular naturally-occurring truncated IL-23Rα protein. The Δ9 protein has 348 amino acids plus eight (8) novel amino acid sequences unique to Δ9 protein (a total of 356 amino acids). The signal sequence (i.e., 1-23 amino acids) on the immature Δ9 protein (located inside the cells) is cleaved before the mature Δ9 protein is released outside of the cells. The mature Δ9 protein therefore has a total of 333 amino acids (i.e., 24-356). The present ELISA assay can specifically detect both of these two (2) Δ9 forms (i.e., immature Δ9 and mature Δ9). For purposes of this application, therefore, the term "Δ9" is intended to include both of these two (2) forms.

As used herein, the term "Δ8,9" refers to the naturally-occurring truncated IL-23Rα resulting from IL-23 gene splicing. The Δ8,9 has 318 amino acids plus eight (8) novel amino acid sequence unique to Δ8,9 (a total of 326 amino acids). The signal sequence (i.e., 1-23 amino acids) on the Δ8,9 is cleaved before the mature Δ8,9 protein is released. Therefore, the mature Δ8,9 has a total of 303 amino acids (i.e., 24-326). For purposes of this application, the term "Δ8,9" is intended to include both of the two (2) forms.

As used herein, the term "detecting" refers to quantitative measurements of IL-23R in a biological sample.

As used herein, the term "biological sample" refers to a body sample from a mammal, preferably from a human. Biological sample may be obtained from patients inflicted with autoimmune diseases. Biological samples include biological fluids such as serum, plasma, lymph fluid, synovial fluid, amniotic fluid, urine, cerebro-spinal fluid, saliva, tissue culture medium, tissue extracts and the like. The preferred biological sample is serum or plasma.

As used herein, the term "capture reagent" refers to a reagent capable of binding and capturing a target molecule in a sample such that under suitable condition, the capture reagent-target molecule complex can be separated from the rest of the sample. Typically, the capture reagent is immobilized. In a sandwich immunoassay, the capture reagent is preferably an antibody or a mixture of different antibodies against a target antigen.

As used herein, the term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. The preferred detectable antibody is biotinylated antibody.

As used herein, the term "detection means" refers to a moiety or technique used to detect the presence of the detectable antibody in the ELISA herein and includes detection agents that amplify the immobilized label such as label captured onto a microtiter plate. Preferably, the detection means is a fluorimetric detection agent such as avidin or streptavidin.

As used herein, the term "antibody" is used in the broadest sense and includes monoclonal antibodies, polyclonal antibodies, multivalent antibodies, multi-specific antibodies, and antibody fragments so long as they exhibit the desired binding specificity.

As used herein, the term "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. Nature 256:495 (1975). The "monoclonal antibodies" may also be isolated from phage antibody libraries using the techniques described in Clackson et al. Nature 352:624-628 (1991) and Marks et al. J. Mol. Biol. 222:581-597 (1991).

The monoclonal antibodies herein may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al. Proc. Natl. Acad. Sci. USA 81:6851-6855 (1984)).

As used herein, the term "mammal" refers to any animal classified as a mammal, including humans, and animals. Preferably, the mammal is a human.

As used herein, the term "autoimmune disease" refers to a pathological condition in mammals that is typically characterized by an unregulated immune cell activity. Examples of autoimmune include but are not limited to, inflammatory bowel disease, Crohn's disease, asthma and the like. Preferably, the autoimmune diseases are characterized by an increased Th17 activity.

As used herein, the term "inflammatory bowel disease" means an inflammatory disease in bowel that involves Th17 cells. Crohn's disease represents an exemplary inflammatory bowel disease.

As used herein, the term "Crohn's disease" is an inflammatory disease of the intestines. It primarily causes abdominal pain, diarrhea (which may be bloody if inflammation is at its worst), vomiting, or weight loss. Crohn's disease is believed to be an autoimmune disease, in which the body's immune system attacks the gastrointestinal tract, causing inflammation.

As used herein, the term "active Crohn's disease" refers to a clinical state where at the time the patient is displaying symptoms of Crohn's disease such as cramping, bloody stool, diarrhea and the like.

As used herein, the term "inactive Crohn's disease patient" refers to a clinical state where at the time the patient (although he/she has been diagnosed as having Crohn's disease) is not displaying symptoms of Crohn's disease such as cramping, bloody stool, diarrhea and the like.

As used herein, the term "intestinal resection" refers to the surgical removal of a part of intestinal tract such as colon.

The present inventors discovered a hitherto unknown soluble form of a human IL-23Rα receptor (e.g., Δ9). Δ9 mRNAs is a result of alternative splicing of the IL-23Rα gene that encodes the native IL-23Rα protein. The splice variant Δ9 is missing the exon 9 and does not contain a transmembrane domain and an intracellular domain. In Δ9, Exon 8 joins to Exon 10 and results in the shift of open reading frame and hence generates the novel eight (8) amino acid sequences (i.e., GLKEGSYC, SEQ ID NO: 7). Δ9 mRNA represents up to 20% of human leukocyte IL-23Rα transcript and thus is a major form of IL-23Rα mRNA. Δ8,9 mRNA also is detectable in the Fragment Analysis studies.

Using an ELISA developed by the present inventors, we detected the Δ9 protein form of IL-23Rα is secreted and present as a soluble monomer in a biological sample. The Δ9 protein form is found to be associated with inflammatory bowel diseases such as Crohn's disease. The Δ9 protein is found to bind to IL-23 in solution. The present inventors further discovered that this soluble IL-23Rα form is capable of blocking IL-23 induced STAT3 phosphorylation and Th17 maturation.

It is known that the native form of human IL-23Rα mRNA is 2.8 kb long, with 11 exons (NM_144701). This mRNA is translated into a typed transmembrane protein of 629 amino acids. The native human IL-23Rα protein comprises an extracellular domain that contains 354-residue extracellular domain that includes a signal peptide, an N-terminal fibronectin-III-like domain, as well as a 253-residue cytoplasmic domain with three potential tyrosine phosphorylation sites. Genetic studies have suggested an association the IL-23Rα locus with protection/susceptibility in autoimmune inflammatory disorders, although the exact mechanistic basis remains elusive.

The present inventors have unexpectedly discovered a novel soluble truncated IL-23Rα. The present invention extends our previous findings that IL-23Rα mRNA undergoes extensive alternative splicing—resulting in twenty-four (24) different potential transcripts. (Kan et al.) Four different classes of putative translation products could be deduced from these alternatively spliced mRNA sequences: (i) short premature IL-23Rα extracellular peptides; (ii) soluble forms of IL-23Rα lacking transmembrane/intracellular domains; (iii) full-length IL-23Rα with a truncated extracellular region and (iv) a membrane bound receptor isoform of IL-23Rα that lacked likely intracellular signaling components.

Using Fragment Analysis, the present inventors surprisingly discovered that there are six (6) alternative splice mRNA forms in human leukocytes. One of the forms (i.e., Δ9) represents the majority alternative splice mRNA form. Δ9 protein is found to be soluble and exists as monomer, and it has the ability to bind p19 and inhibit the generation of functional human Th-17 cells in vitro. Different from that of the native IL-23Rα protein, the present soluble truncated IL-23Rα lacks a transmembrane domain and contains 356 amino acids. Another form (i.e., Δ8,9) also share the common features as Δ9 (e.g., soluble monomer and ability to block IL-23R mediated cell signaling).

According to the present invention, the recombinant IL-23Rα (which is a soluble truncated form of IL-23Rα protein) contains a unique eight (8) amino acid sequence (GLKEGSYC) (SEQ ID NO: 7) at its C-terminus (in the proximity of the transmembrane domain) due to the alternative translation reading frame on exon 10. When analyzed under conditions of a reducing gel electrophoresis, the molecular weight of the protein is approximately ~65 kDa. The soluble truncated recombinant protein corresponds to a N-terminal fragment of IL-23Rα lacking the transmembrane domain and has 356 amino acids (with 348 amino acids correspond to that of the native IL-23Rα). The amino acid sequence of the soluble truncated IL-23Rα is set forth in SEQ ID NO: 2.

According to the present invention, the soluble truncated recombinant IL-23Rα form of Δ8,9 also contains a unique eight (8) amino acid sequence (GLKEGSYC) (SEQ ID NO: 7) at its C-terminus, in the proximity of the transmembrane domain, due to the exon 8 and exon 9 skipping. When analyzed under conditions of a reducing gel electrophoresis, the molecular weight of the protein is approximately ~60 kDa. The soluble truncated IL-23Rα protein (Δ8,9) corresponds to a N-terminal fragment of IL-23R lacking the transmembrane domain and has 356 amino acids (with 348 amino acids correspond to that of the native IL-23Rα). The amino acid sequence of the soluble truncated IL-23Rα is set forth in SEQ ID NO: 4.

In one embodiment, the present invention provides an isolated IL-23Rα protein that includes the protein selected from any of the following protein, an isolated protein of a truncated human IL-23Rα capable of inhibiting IL-23-mediated cell signaling; a recombinantly produced truncated human IL-23Rα; or a purified recombinant human truncated IL-23Rα having an amino acid sequence set forth in SEQ ID NO: 2 and SEQ ID NO: 4.

The soluble truncated IL-23Rα exists as a monomer and contains a unique eight (8) amino acid sequence. In one embodiment, the soluble IL-23Rα is detected in cultured media and can be recombinantly produced. The isolated truncated IL-23Rα protein has therapeutic value to alleviate inflammatory bowel diseases including Crohn's disease.

In a preferred embodiment, the present invention provides a recombinant soluble IL-23Rα, which has the amino acid sequence set forth in SEQ ID NO: 2 and SEQ ID NO: 4.

The present invention provides an isolated nucleic acid molecule encoding a truncated human IL-23Rα protein lacking a transmembrane domain. In one embodiment, the isolated nucleic acid molecule is a DNA, preferably the isolated DNA is genomic DNA. In another embodiment, the isolated DNA molecule is a cDNA molecule. In one embodiment, the isolated nucleic acid molecule is an RNA molecule. In an embodiment, the isolated nucleic acid molecule encodes a human IL-23Rα having an amino acid sequence set forth in SEQ ID NO: 2, wherein the nucleotide sequence of the isolated DNA molecule is set forth in SEQ ID NO: 1. In an embodiment, the isolated nucleic acid molecule encodes a human IL-23Rα having an amino acid sequence set forth in SEQ ID NO: 4, wherein the nucleotide sequence of the isolated DNA molecule is set forth in SEQ ID NO: 3.

The present invention provides a recombinantly produced human IL-23Rα lacking a transmembrane domain. The present invention provides a purified recombinant human truncated IL-23Rα having the amino acid sequence set forth in SEQ ID NO: 2 or SEQ ID NO: 4.

In one embodiment, the present invention provides an ELISA to aid detecting the circulating level of the soluble truncated IL-23Rα protein. One of ordinary skill in the art would recognize the use of commercially-available antibodies in the present developed Δ9 ELISA. Using an ELISA, it is demonstrated that Δ9 protein is present at low levels in the periphery of healthy individuals. Similarly, the present inventors believe that Δ8,9 are present in patients suffering from inflammatory bowel diseases. Soluble cytokine receptors may be generated by several mechanisms, including proteolytic cleavage of receptor ectodomains, alternative splicing of mRNA transcripts or transcription of distinct genes. The present inventors believe that Δ9 (and Δ8,9) present in the circulation is solely a result of alternative splicing of the native IL-23Rα mRNA. Given the human genome project is completed, it is believed that it is highly unlikely that there is a distinct gene encoded for a soluble form of IL-23Rα chain.

The present invention also includes a kit for carrying out the methods of the invention. The subject kit comprises a first antibody specific for a carboxyl-truncated region of IL-23Rα. In one embodiment, the first antibody is a monoclonal antibody. Preferably, the first antibody recognizes and binds to the carboxyl terminus of Δ9 isoform of IL-23Rα. More preferably, at or near exon 8 (i.e., amino acid residues 318-348).

In one embodiment, the kit comprises a second antibody. In one embodiment, the second antibody is a polyclonal antibody. Preferably, the second antibody recognizes and binds to the extracellular domain of the Δ9 isoform of IL-23Rα. Preferably, the binding site of the first antibody does not overlap with that of the second antibody.

In other embodiments, the second antibody contains a labeling component. Such labeling component includes a detection means. One of ordinary skill in the art would appreciate the detection means to include streptavidin conjugated with horseradish peroxidase (HRP), which specifically binds biotin on the detection antibody. The peroxidase activity (representing the level of Δ9) was measured by addition of tetramethylbenzidine (TMB) substrate.

In one embodiment, the present kit can further include, if desired, one or more of various conventional components, such as, for example, containers with one or more buffers, detection reagents or antibodies. Printed instructions, either as inserts or as labels, indicating quantities of the components to be used and guidelines for their use, can also be included in the kit.

The present kit may further comprises a detection antibody, which is either directly or indirectly detectable, and which binds and allows the quantification of the relative carboxyl-terminal truncated IL-23Rα levels.

The present kit may also contain a control full-length recombinant full-length and Δ9 IL-23Rα dilution series, where the dilution series represents a range of appropriate standards with which a user of the kit can compare their results and estimate—the level of Δ9 IL-23Rα in their sample. Fluorescence or color development results may also be compared to a standard curve of fluorescence or color density provided by the kit.

The present invention will be better understood from the following experimental studies. One of ordinary skill in the art would readily appreciate that the specific methods and results discussed therein are not intended to limit the invention. The experimental studies merely serve illustrative purposes, and the invention is more fully described by the claims which follow thereafter.

EXPERIMENTAL STUDIES

Example 1

Generation of Splice Variant Forms of IL-23Rα

In this series of study, we generated IL-23Rα constructs for wild-type (WT) and four (4) IL-23Rα isoforms. These IL-23Rα constructs include WT, Δ8, Δ9, Δ8,9, and pΔ11 IL-23 isoforms (FIGS. 1 and 2):

(i) WT represents wild-type IL-23Rα. It contains 629 amino acids. 1-353 amino acids are the extracellular domain. 377-629 amino acids are the cytoplasmic domain. The transmembrane domain is encoded in the amino acids from 354 to 376. The first 23 amino acids represent the signal sequence (a.a. 1-23).

(ii) pΔ11 represents a partial deletion of exon 11. This partial deletion results in frame shift and thus generates the pre-mature translational termination signal. The pΔ11 protein contains the amino acids from 1 to 413. Due to the frame shift, pΔ11 protein contains a novel amino acid "R" at the C-terminal end.

(iii) Δ8 represents the deletion of exon 8 and is an in-frame deletion. Δ8 variant used the same translation termination signal at exon 11 as that of the wild-type IL-23Rα. The Δ8 protein contains amino acids from 1 to 318 fused to amino acids from 350 to 629. Therefore, the Δ8 protein has internal deletion from amino acid 319 to 349, which is encoded by exon 8.

(iv) Δ9 represents the deletion of exon 9. This exon 9 deletion results in frame shift and thus generates the pre-mature translational termination signal at exon 10. The Δ9 protein contains the amino acids from 1 to 348. Due to the frame shift, the Δ9 protein contains 8 novel amino acids "GLKEGSYC" at the C-terminal end.

(v) Δ8,9 represents the deletion of exon 8 and exon 9. The exon 8 and 9 deletions result in frame shift and thus generates the pre-mature translational termination signal at exon 10. The Δ8,9 protein contains the amino acids from 1 to 318. Due to the frame shift, the Δ8,9 protein contains 8 novel amino acids "GLKEGSYC" at the C-terminal end.

All five (5) IL-23Rα expression constructs were constructed by PCR amplification. The expression constructs were cloned into pcDNA3.3 expression vector using TOPO cloning (Invitrogen). Correct nucleotide sequences of all the expression constructs were confirmed by DNA sequencing.

Figure 2:
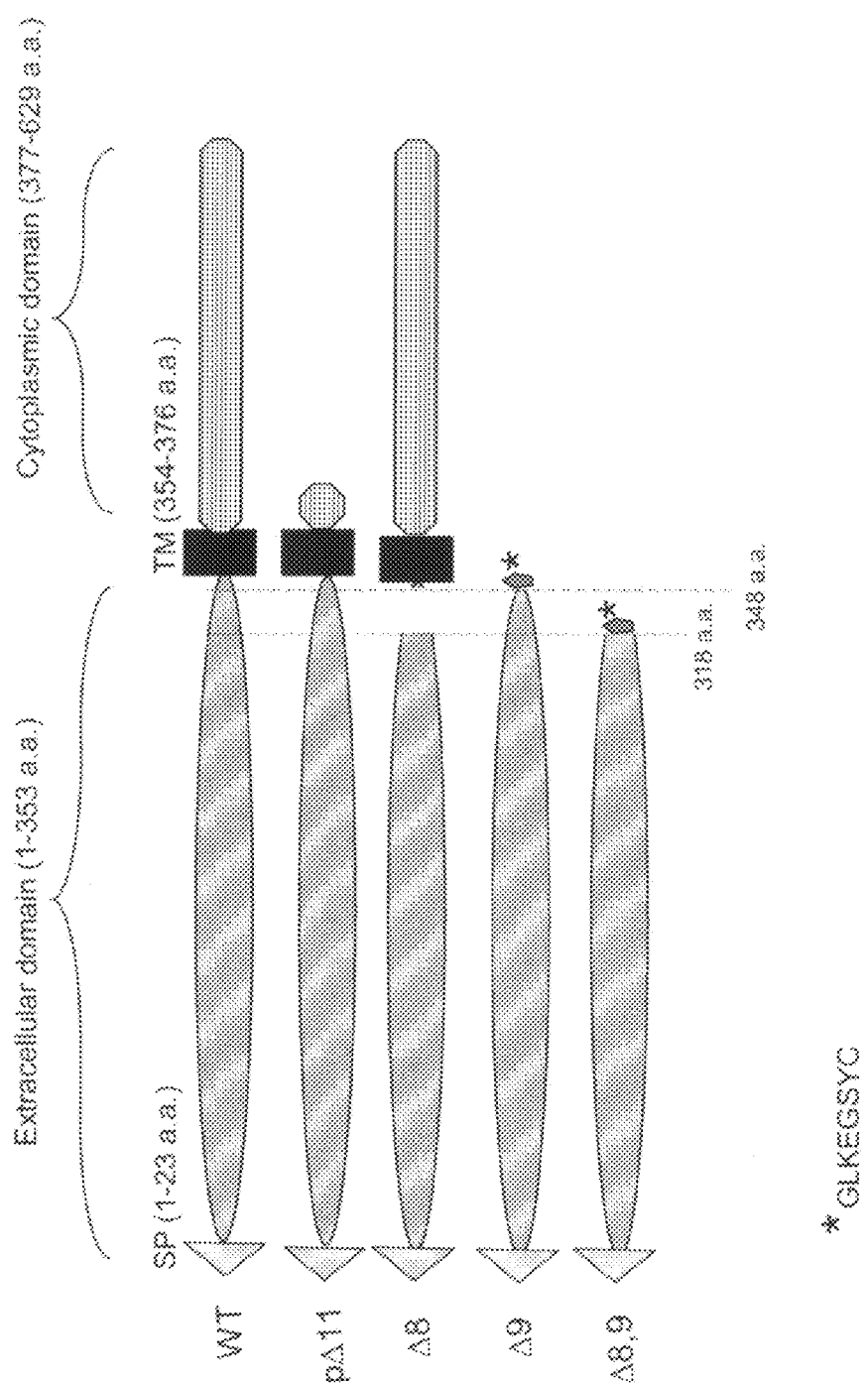
FIG. 2 depicts the domain organization of the expressed IL-23Rα proteins. Wild-type IL-23Rα contains signal peptide at its N-terminus followed by extracellular domain, transmembrane region and cytoplasmic domain. Partial deletion of exon 11 (pΔ11) caused removal of almost entire cytoplasmic domain. Deletion of exon 8 (Δ8) resulted in internal removal of C-terminal region of extracellular domain while the transmembrane region and cytoplasmic domain remained intact. Deletion of exon 9 (Δ9) and deletion of exon 8 and 9 (Δ8,9) both resulted in complete removal of transmembrane region and cytoplasmic domain. Therefore, Δ9 and Δ8,9 were predicted to be secreted proteins. Δ9 protein contained the extracellular domain from amino acids 1 to 348 whereas Δ8,9 protein contains extracellular domain from amino acids 1-318. All the expressed proteins were tagged with Flag epitope at C-terminus for detection purpose using Anti-Flag M2 antibody.

The domain organization of the expressed IL-23Rα proteins is summarized in FIG. 2. The wild-type IL-23Rα contains a signal peptide (amino acid 1-23) at its N-terminus followed by an extracellular domain (amino acid 24-353), transmembrane region (amino acid 354-376), and cytoplasmic domain (amino acid 377-629). Deletion of exon 8 (Δ8) results in an internal removal of C-terminal region of extracellular domain while the transmembrane region and the cytoplasmic domain remains intact. Partial deletion of exon 11 (pΔ11) results in the truncation of cytoplasmic domain but leaves both extracellular domain and transmembrane region intact. Deletion of the exon 9 (Δ9) and deletion of the exons 8 and 9 (Δ8,9) both result in the complete removal of a transmembrane region and cytoplasmic domain. Thus, Δ9 and Δ8,9 are predicted to be secreted proteins.

Δ9 IL-23Rα protein contains the extracellular domain (amino acid 1-348) whereas Δ8,9 IL-23Rα protein (amino acid 1-318) has deletion at the C-terminal region of the extracellular domain.

The IL-23Rα expression constructs were transfected into a mammalian cell (i.e., 293T cells). The expressed IL-23Rα proteins were prepared for subsequently use to study the specificity of anti-hIL-23Rα antibodies. All the expressed proteins are tagged with Flag epitope at the C-terminus for detection purpose using an anti-Flag M2 antibody (Sigma).

Example 2

Expression of IL-23Rα Constructs

We performed the transient transfection of the IL-23Rα expression constructs into 293T cells by Fugene HD. Cell lysates were prepared after 48 hours of post-transfection. Cultured media were also collected.

Expression levels of the wild-type IL-23Rα and its four (4) variants were examined by immunoblot using anti-Flag M2 antibody. All expression constructs produced similar level of proteins in the cell lysates (FIG. 3 Top panel).

Figure 3:
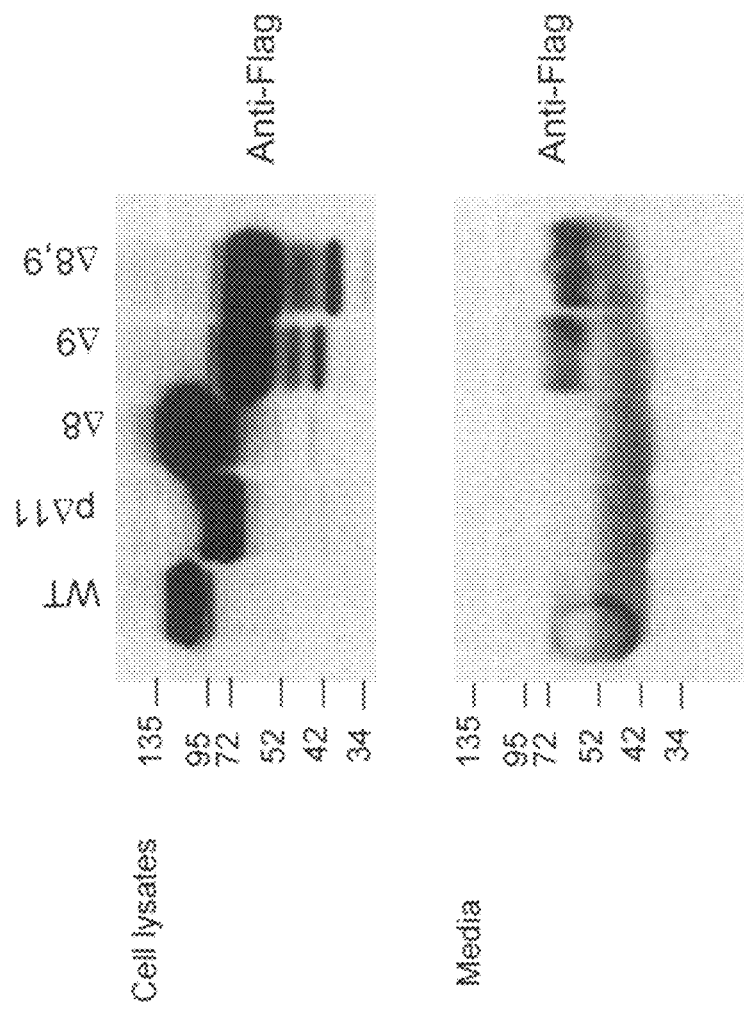
FIG. 3 depicts the transient transfection of the IL-23Rα expression constructs into 293T cells by Fugene HD. Cell lysates were prepared after 48 hours post-transfection. Cultured media were also collected. Expression levels of wild-type IL-23Rα and its variants were examined by immunoblot using Anti-Flag M2 antibody. All expression constructs produced similar level of proteins in the cell lysates. However, only Δ9 and Δ8,9 were found in the cultured media, which demonstrated that these two proteins are actively secreted out of the cells.

Noted that only Δ9 (amino acid 1-348) and Δ8,9 (amino acid 1-318) were found in the cultured media, indicating that these two proteins are actively secreted from the cells (FIG. 3 Bottom panel).

Example 3

ELISA Development

Using the cellular lysates as described in Example 2, we proceeded to develop a Sandwich ELISA system. The ELISA system allows detection of the soluble form of human IL-23Rα (Δ9). In this ELISA system, two anti-hIL-23Rα antibodies are required, each recognizing different epitopes on IL-23Rα. The cell lysates obtained from the transient transfection experiment (Example 2) were used to examine the antibody specificity and epitope mapping.

a) Capture Antibody

Figure 4:
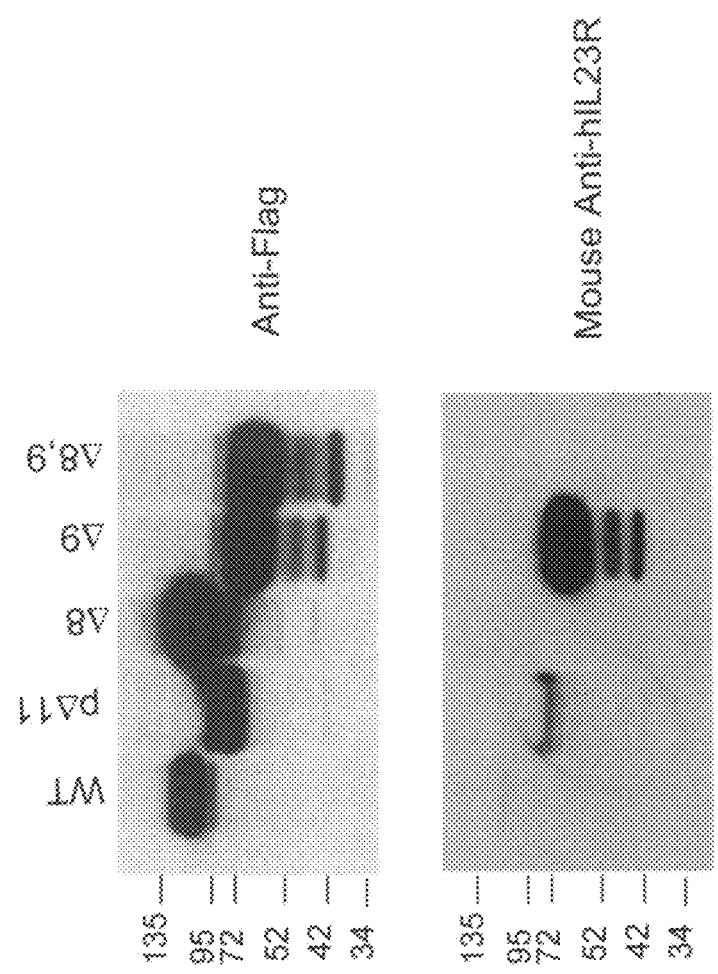
FIG. 4 depicts the specificity of the mouse anti-hIL-23Rα antibody. Cell lysates prepared from the 293T transient transfection experiment (by Fugene HD) were used in the immunoblot assay. The mouse anti-hIL-23Rα antibody recognized wild-type IL-23Rα (weakly), pΔ11 and Δ9. More importantly, this antibody was highly sensitively to Δ9. However, this antibody failed to detect Δ8 and Δ8,9 proteins indicating that the antibody recognized the C-terminal region of extracellular domain (amino acids 319-348) encoded by the exon 8.

Mouse anti-hIL-23Rα antibody (R&D Systems) was used in the immunoblot assay. This antibody recognizes the wild-type IL-23Rα, pΔ11 and Δ9. More importantly, this mouse anti-hIL-23Rα antibody is found to be highly sensitively to Δ9 (FIG. 4 Bottom panel). Therefore, this antibody was used as a capture antibody in our ELISA system.

Because this antibody fails to detect Δ8 and Δ8,9 proteins, it indicates that the antibody recognizes the C-terminal region of extracellular domain encoded by exon 8 (amino acid from 319 to 348).

Figure 5:
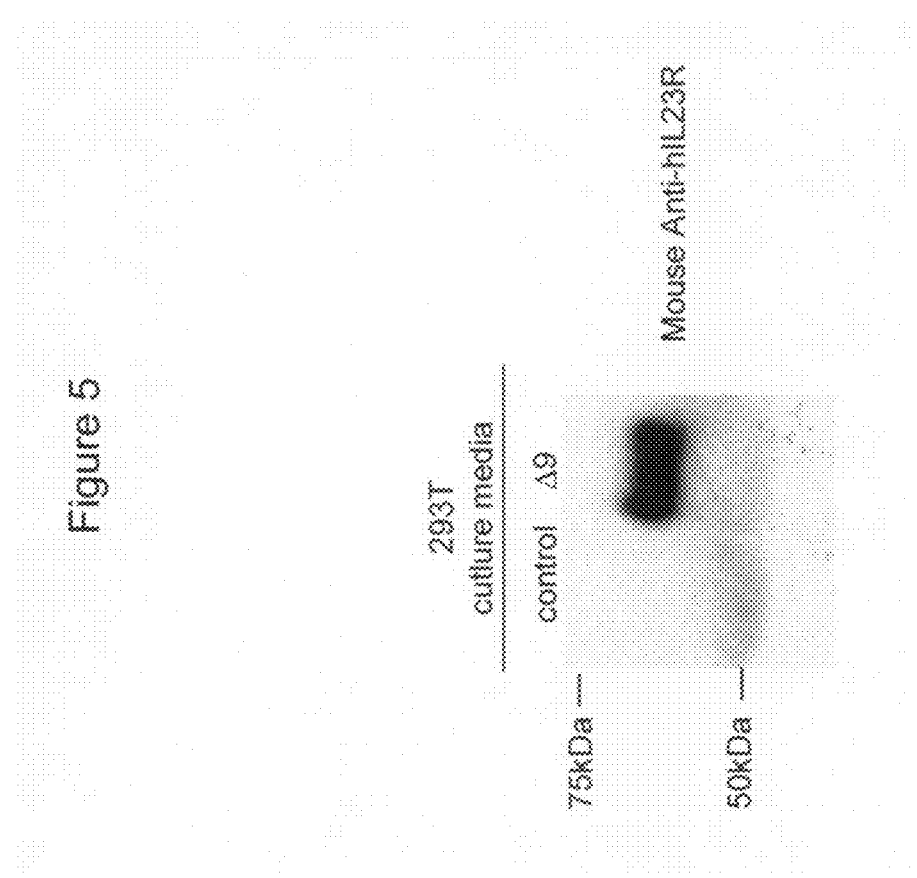
FIG. 5 depicts an immunoblot experiment using a mouse anti-hIL-23Rα (anti-human IL-23Rα) antibody to detect the soluble recombinant Δ9 protein in the culture media obtained from 293T cells transfected with either control plasmid or Δ9 expression plasmid.

Since Δ9 is a secreted protein, we also performed an experiment to show that this mouse antibody is capable to recognize the secreted Δ9 in the 293T cell culture medium transfected with Δ9 expression construct (FIG. 5). This result indicates that this mouse antibody detects not only the intracellular Δ9 but also secreted Δ9.

In addition to the commercially available mouse anti-hIL-23Rα antibody (R&D Systems), we also prepared different mouse monoclonal antibodies targeted against human IL-23Rα protein (i.e., amino acid residues 116-129). Synthetic peptides covering this region were used as antigen and injected into mice to prepare monoclonal antibodies. Several hybridoma cells were generated. We selected four (4) hybridoma cells and obtained purified monoclonal antibodies from these hybridoma supernatants. All these hybridomas show avid binding (i.e., high affinity) to the peptide antigen (i.e., amino acid residues 116-129).

The four (4) hybridoma clones were identified as 2C8E10, 2C8C4, 3A5C11 and 3A5D11. Monoclonal antibodies secreted by these hybridoma cells were further purified using Protein A resin (standard protocol). The purified monoclonal antibodies were tested in two (2) different validation assays: namely (i) immunoprecipitation and (ii) ELISA.

All four (4) monoclonal antibodies were shown to immunoprecipitate Δ9 protein. Immunoprecipitation was performed using standard protocol (See "Materials & Methods).

Two (2) of the purified monoclonal antibodies from hybridoma cells (i.e., 3A5C11 and 3A5D11) were tested using our ELISA. Instead of using the commercially available mouse anti-hIL-23Rα antibody from R&D as the capture antibody, we used our purified monoclonal antibodies (i.e., 3A5C11 and 3A5D11) in the ELISA to measure the amount of soluble human IL-23Rα. We found that both of our monoclonal antibodies are capable of capturing soluble human IL-23Rα similar to the commercially available mouse anti-hIL-23Rα antibody (See Table below).

TABLE 1

Characterization of our prepared monoclonal antibodies

| Clone IDs: | Immunoprecipitation | ELISA as Capture Antibody |
|---|---|---|
| 2C8E10 | Yes | N.D. |
| 2C8C4 | Yes | N.D. |
| 3A5C11 | Yes | Yes |
| 3A5D11 | Yes | Yes | b) Detection Antibody

Goat anti-human IL-23Rα was used as a detection antibody. The goat anti-human IL-23Rα is preferably in biotinylated form.

Figure 6:
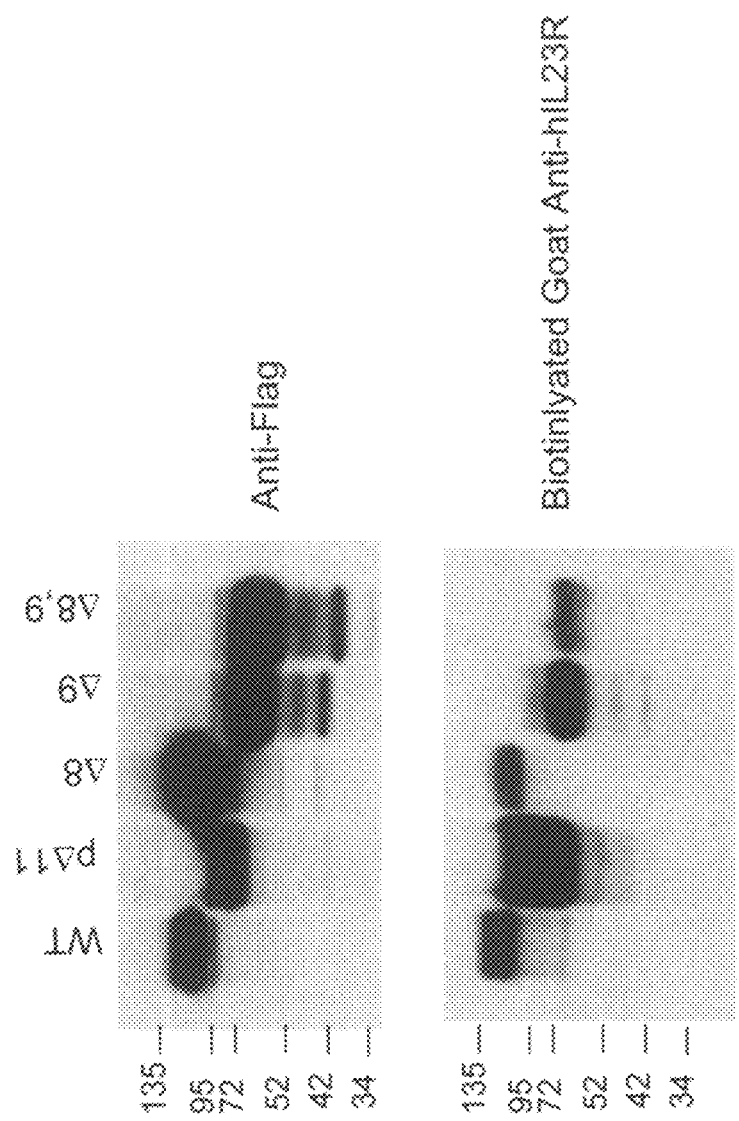
FIG. 6 depicts the specificity of biotinylated goat anti-hIL-23Rα antibody in the immunoblot experiment using cellular lysates from the 293T cells transfected with five (5) different expression plasmids hosting wild-type hIL-23Rα, pΔ11, Δ8, Δ9, and Δ8,9. All the recombinant proteins were tagged with Flag sequence at the C-terminus. The top panel was the immunoblot experiment using anti-Flag antibody to show that all the recombinant proteins were expressed at comparable level. The bottom panel was the immunoblot experiment using biotinylated goat anti-IL-23Rα antibody.

We examined the specificity of the biotinlyated goat anti-human IL-23Rα (FIG. 6 Bottom). We also performed the immunoblot assay using anti-Flag to show that all the recombinant proteins expressed at a similar level (FIG. 6 Top). This goat antibody detects all the expressed proteins. More importantly, the goat antibody recognizes a different epitope from that of the mouse antibody.

As such, the mouse and goat anti-hIL-23Rα antibodies were used as a "match antibody pair" in the ELISA. The mouse antibody was used as the capture antibody because of its high sensitively to Δ9, whereas the biotinlyated goat antibody was used for detection. Goat anti-hIL-23Rα (R&D Systems) was used as a detection antibody. The goat anti-hIL-23Rα is preferably in biotinylated form.

c) Sandwich ELISA

Figure 7:
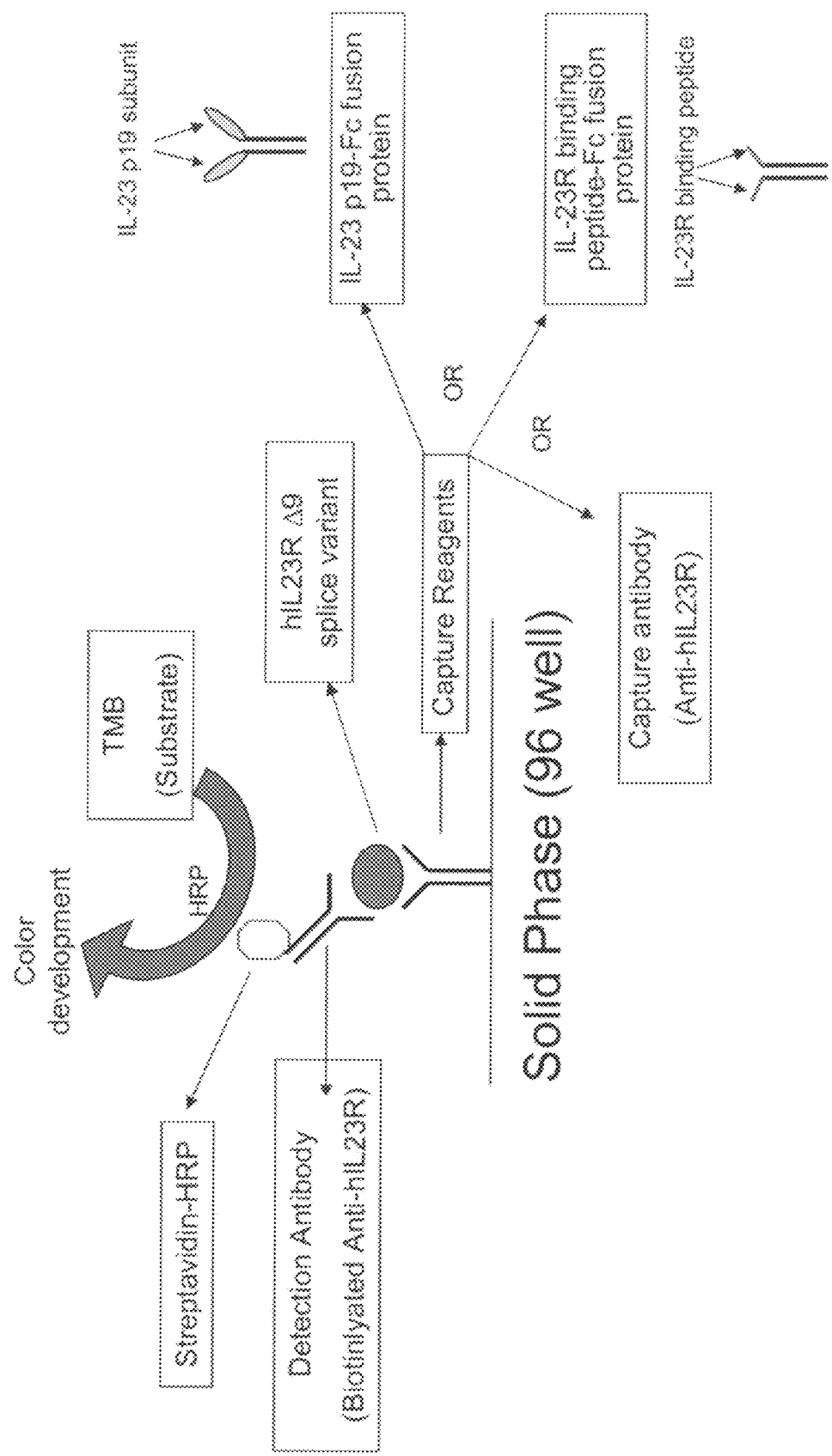
FIG. 7 depicts the ELISA sandwich system. The capture reagents can be either be anti-hIL-23Rα antibody, IL-23 p19 subunit fused to Fc region of IgG or IL-23Rα binding peptide fused to Fc region of IgG. The capture reagents were coated on the solid support (e.g., microtiter plate) to capture the soluble form of the IL-23Rα. The capture antibody specifically captured the soluble IL-23Rα on the ELISA plate. The captured soluble IL-23Rα was then detected by a biotinlyated goat anti-hIL-23Rα antibody. The antibody-antigen sandwich was detected by streptavidin conjugated with horseradish peroxidase (HRP). The peroxidase activity (representing the level of Δ9) was measured by addition of tetramethylbenzidine (TMB) substrate. The color intensity was in direct proportion to the amount of the bound IL-23Rα. Color development was stopped and the intensity of the color was measured at optical density (OD) 450 nm on a microtiter plate reader.

FIG. 7 depicts the Sandwich ELISA to detect the soluble form of IL-23Rα (Δ9). In this particular example, the ELISA uses 2 different anti-hIL-23Rα antibodies. The mouse anti-hIL-23Rα antibody was used as capture antibody and coated on the solid support (e.g., microtiter plate) to capture the soluble form of the IL-23Rα (Δ9). Because the mouse antibody only detected the soluble IL-23Rα containing amino acids from 319 to 348 and Δ9 is the only secreted variant containing this amino acid sequence among other known secreted variants, this antibody specifically captured the Δ9 variant on the ELISA plate.

The capture of Δ9 IL-23Rα was then detected by a biotinlyated goat anti-hIL-23Rα antibody. The goal anti-hIL-23Rα antibody recognizes a different epitope than that of mouse anti-human I-23R antibody.

Alternatively, other capture reagents such as IL-23 p19 subunit fused to Fc region of IgG or IL-23R binding peptide fused to Fc region of IgG can be used as a substitute for capture antibody (in this particular example, mouse anti-hIL-23Rα antibody). This modified ELISA system involves binding of cytokine (p19-Fc) or peptide (peptide-Fc) to the soluble form of 23Rα (Δ9).

Figure 8:
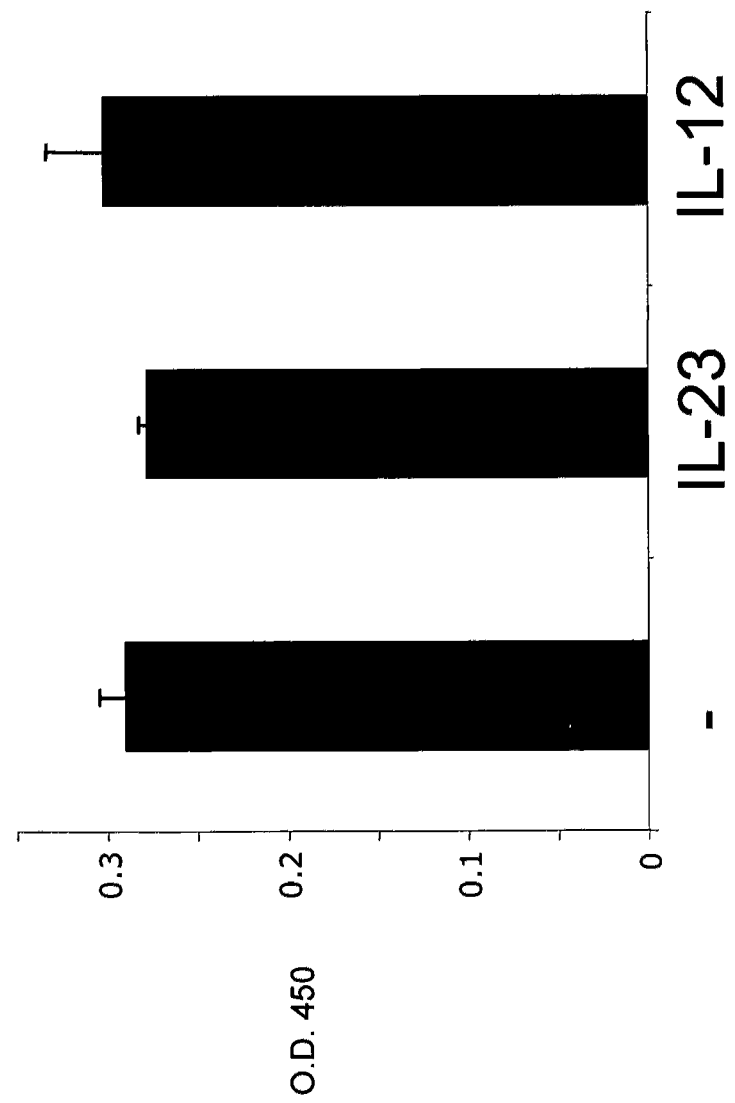
FIG. 8 depicts the ELISA assay result. The ELISA was performed using the culture media containing Δ9 protein or the same culture media spiked with either 100 ng IL-23 or 100 ng IL-12 (negative control). The presence of IL-23 or IL-12 gave same ELISA signal as that in the absence of the spike. This result suggested that binding of IL-23 to Δ9 protein or the presence of IL-12 do not influence the ELISA assay to detect Δ9 protein.

In order to prove that the cytokine binding to the soluble form of the IL-23Rα (Δ9) did not interfere the ELISA detection by the detection antibody, ELISA was performed using capture and detection antibodies. Either nothing, IL-23 (100 ng) or IL-12 (100 ng) was added to the medium containing Δ9 protein. The result clearly shows that cytokine (IL-23) binding to receptor (Δ9) does not interfere the ELISA detection. Therefore, this observation supports our idea that the other capture reagents can be used as the substitute for capture antibody (FIG. 8).

d) Detection System

The antibody-antigen sandwich was detected by strepta-vidin conjugated with horseradish peroxidase (HRP), which specifically binds biotin on the detection antibody. The peroxidase activity (representing the level of Δ9) was measured by addition of tetramethylbenzidine (TMB) substrate. The color intensity was in direct proportion to the amount of the bound IL-23Rα. Color development was stopped and the intensity of the color was measured at optical density (OD) 450 nm on a microtiter plate reader.

Example 4

ELISA Optimization a) Antibody Concentrations

Figure 9:
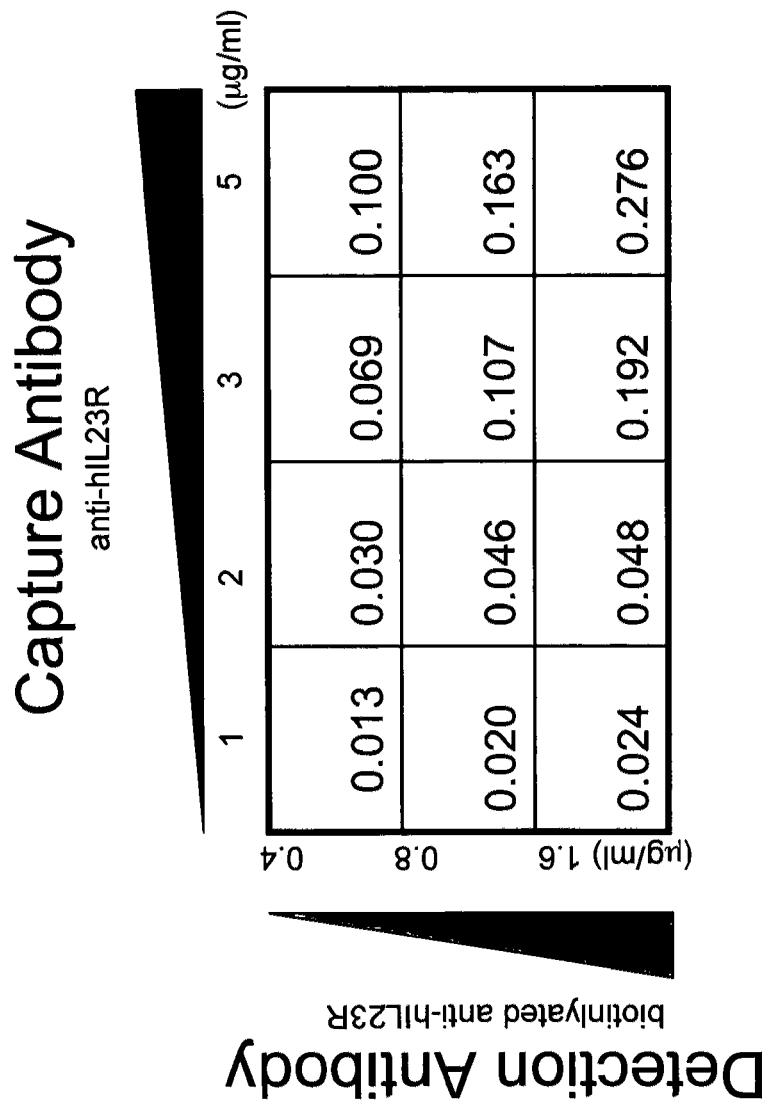
FIG. 9 depicts the optimization of ELISA. Different concentrations of capture and detection antibodies were used to detect 100 ng of antigen, which is a recombinant protein containing entire extracellular domain of hIL-23Rα fused with Fc region of human IgG1 obtained from R&D systems. The combination of capture antibody at 5 μg/ml and detection antibody at 1.6 μg/ml gave the best signal in the ELISA when antigen was incubated at room temperature for 2 hours.

In this series of study, we optimized the ELISA system. Different concentrations of capture and detection antibodies were used to detect the antigen (100 ng), which represents a recombinant protein containing entire extracellular domain of human IL-23Rα fused with Fc region of human IgG1 (obtained from R&D Systems). The combination of capture antibody at 5 µg/ml and detection antibody at 1.6 µg/ml yielded an optimal signal in the ELISA when antigen was incubated at room temperature (25° C.) for 2 hours (FIG. 9).

b) Incubation Temperature and Duration

Figure 10:
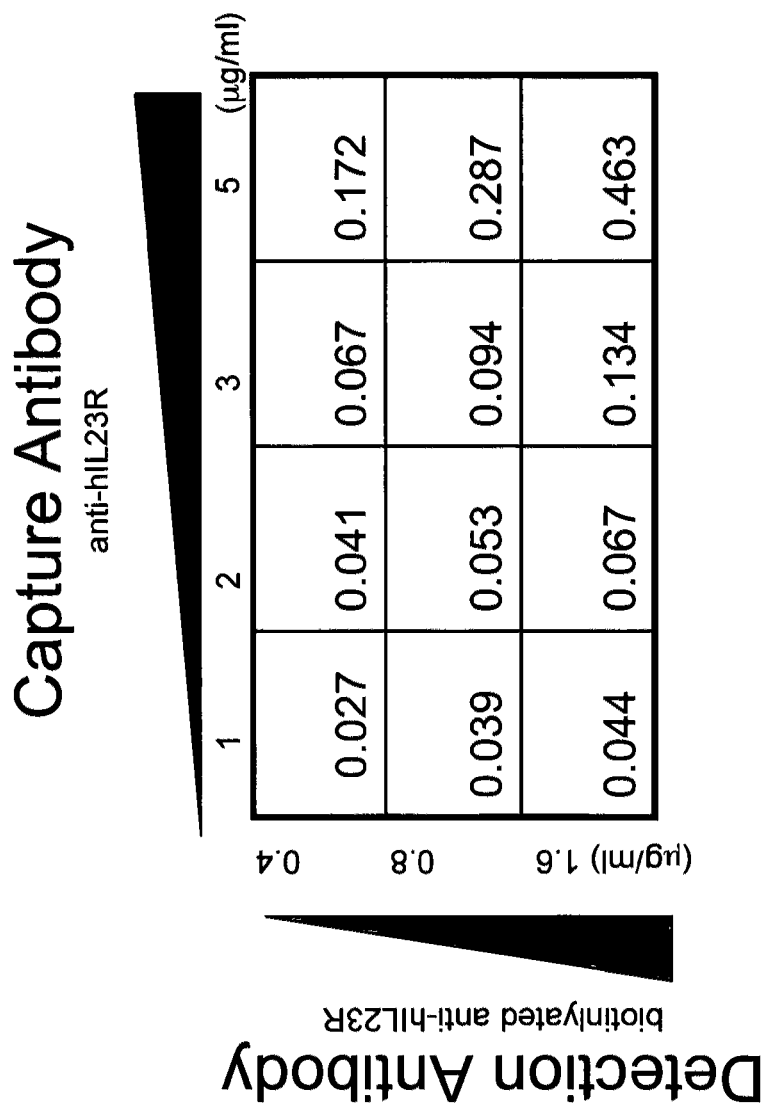
FIG. 10 depicts a titration experiment on capture and detection antibodies with extended antigen incubation (4° C. for 16 hours).

We conducted a titration experiment on capture and detection antibodies with extended antigen incubation (FIG. 10). Antigen incubation time was increased to 16 hours at 4° C. Prolonged incubation at 4° C. further enhanced the sensitivity of the ELISA. Capture antibody was used at 5 µg/ml and detection antibody was used at 1.6 µg/ml. Antigen and sample were incubated at 4° C. for 16 hours.

Figure 11:
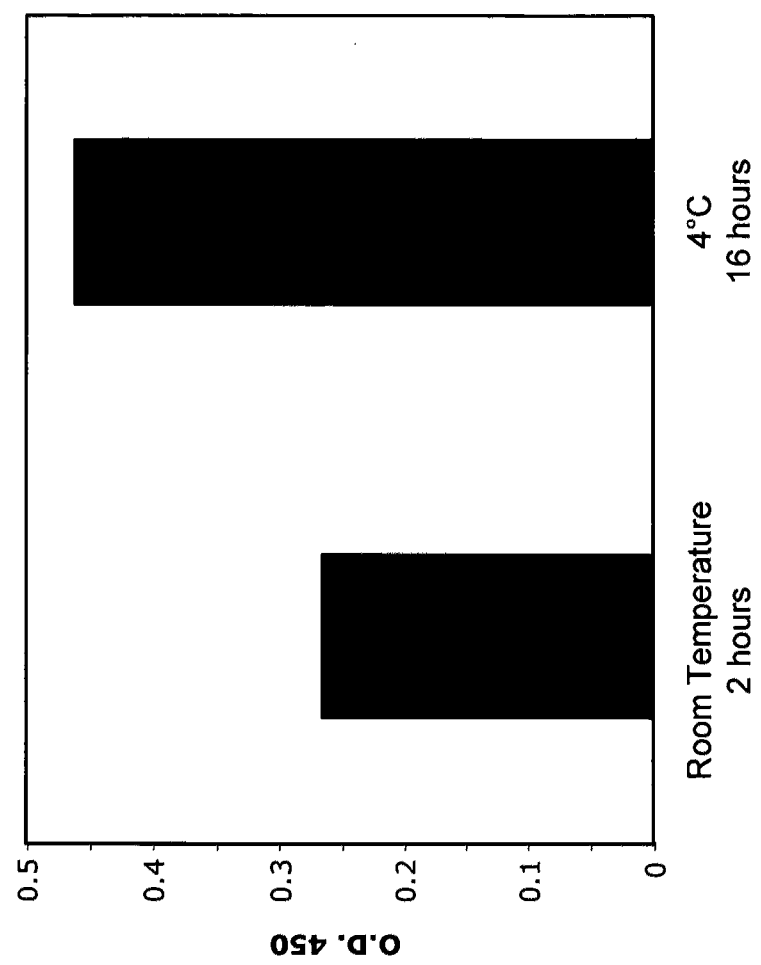
FIG. 11 depicts two (2) different incubation conditions for antigen when capture antibody at 5 μg/ml and detection antibody at 1.6 μg/ml were used.

FIG. 11 depicts two different incubation conditions for antigen when capture antibody at 5 µg/ml and detection antibody at 1.6 µg/ml were used. Incubation of antigen at 4° C. for 16 hours increased the signal by ~67% as compared to that at room temperature for 2 hours.

c) Coating Buffer

Figure 12:
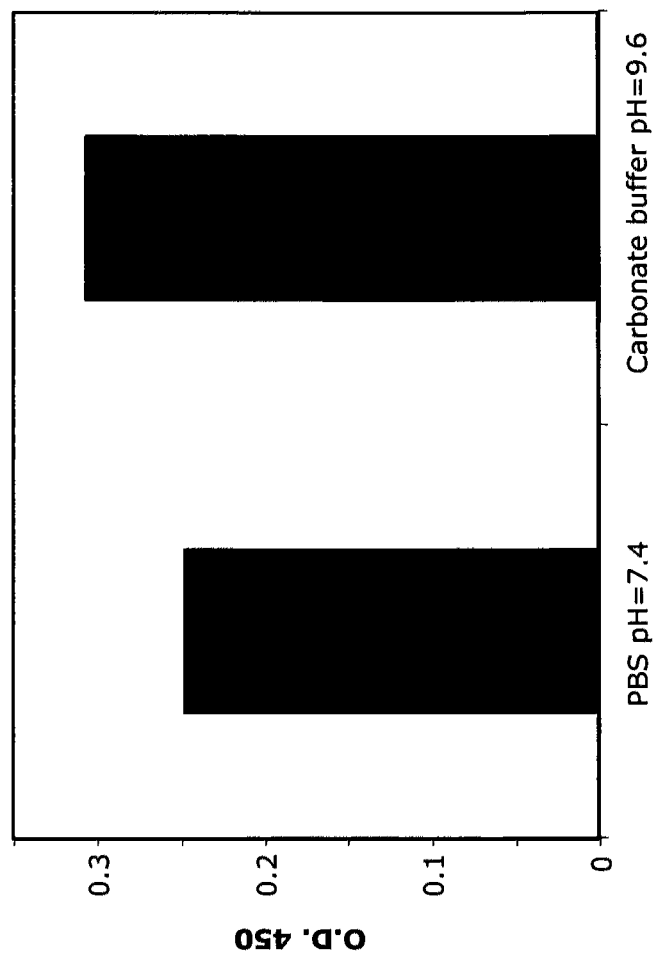
FIG. 12 depicts two (2) different coating buffer conditions (i.e., PBS and carbonate buffer) when capture antibody at 5 μg/ml and detection antibody at 1.6 μg/ml were used.

FIG. 12 depicts the optimization of the coating buffer. Because of the hydrophobic nature of the polystyrene surface, adsorption was allowed to take place at a pH at or slightly above the pI. At such pH, there is no net charge on the protein so as to avoid any potential electrostatic repulsion between the protein and the antibody that is adsorbed on the polystyrene surface. Two commonly used coating buffers were tested (i.e., 50 mM carbonate pH 9.6 and 10 mM PBS pH 7.2). This step was performed at 4° C. overnight (i.e., 16-18 hours) to ensure sufficient adsorption and minimal well-to-well variations. The result indicates that the carbonate buffer (pH 9.6) used yielded a better signal than that of the PBS buffer (pH 7.2).

Example 5

Validation of ELISA Using Purified Δ9 Proteins a) Purification of Recombinant Δ9 Protein from the Transient Transfected 293T Cells We transfected a mammalian cell (i.e., human embryonic kidney fibroblast cell; 293T cell) with either the expression vector alone or the expression vector carrying the Δ9 cDNA. Cell lysates and culture media were prepared and collected for the purification purpose (see "Materials & Methods").

Cells were lysed and cellular lysates were prepared. Δ9 was then immuno-purified using an anti-Flag M2 affinity gel (Sigma). The immuno-precipitated Δ9 was eluted by incubated with excess amount of Flag peptide (see Method). The purity of Δ9 was assayed by SDS-PAGE gel followed by Coomassie-blue staining.

Figure 13:
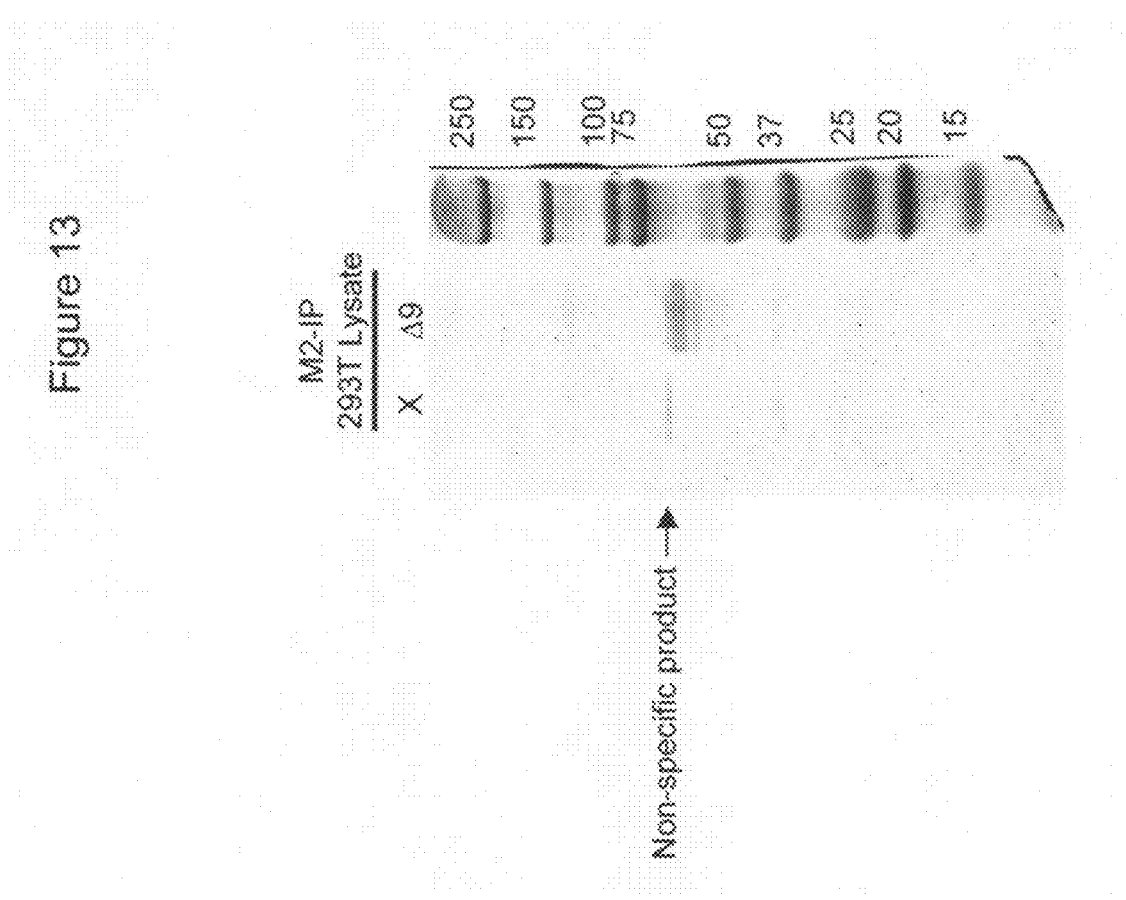
FIG. 13 depicts the purified recombinant Δ9 protein from the intracellular source (i.e., cell lysates from 293T) on the SDS-PAGE gel stained with the Coomassie blue to reveal the purity and estimate the quantity.

No specific band was detected from 293T cell lysate transfected with empty vector, whereas Δ9 protein purified from the cell lysate transfected with Δ9 expression plasmid showed multiple bands (FIG. 13).

Figure 14:
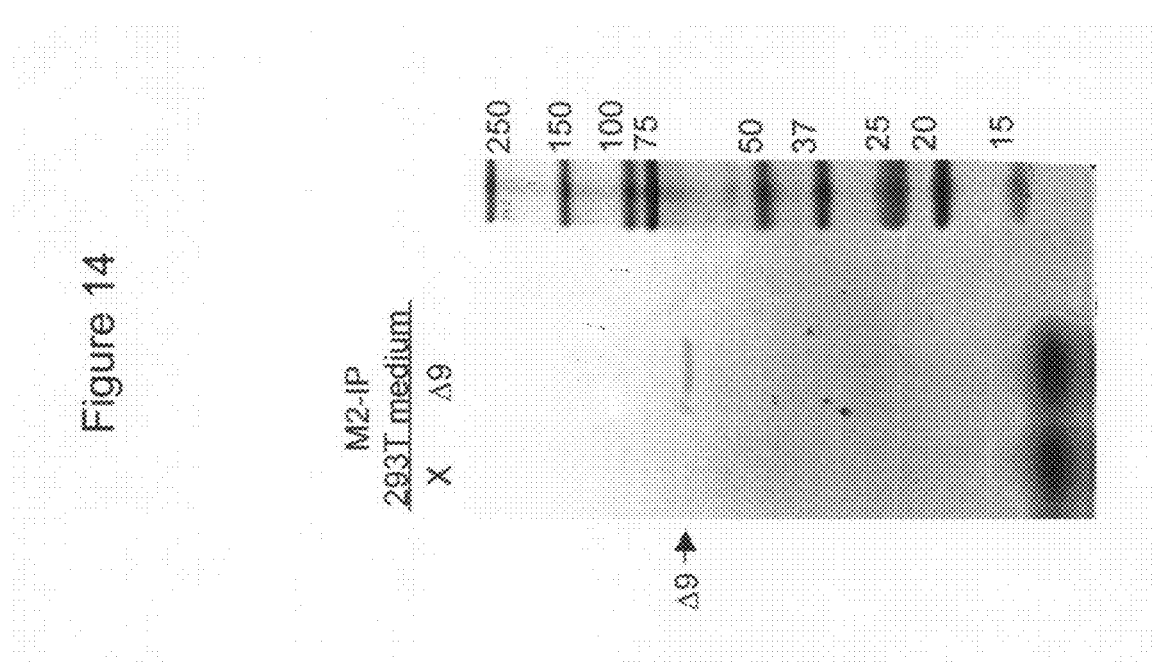
FIG. 14 depicts the purified recombinant Δ9 protein from the secreted source (i.e., culture medium from 293T) on the SDS-PAGE gel stained with the Coomassie blue to reveal the purity and estimate the quantity.

We also performed the purification experiment using the culture media from the 293T cells transfected with empty vector or Δ9 expression plasmid. No protein was detected from 293T cell lysate transfected with empty vector, whereas the purified Δ9 protein from secreted source (culture media) showed a homogenous population as a single band of ~65 kDa in size (FIG. 14).

Figure 15:
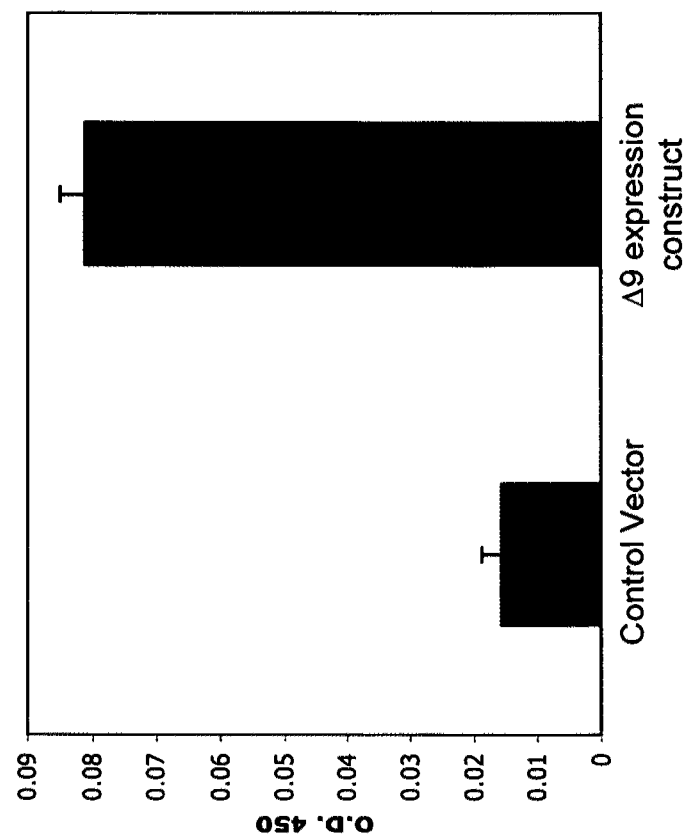
FIG. 15 depicts the validation of developed ELISA using purified recombinant Δ9 protein from whole cell lysates prepared from 293T cell transfected with Δ9 expression plasmid.

FIG. 15 depicts the developed ELISA is validated by using purified Δ9 protein. Δ9 protein purified from cellular lysate was used (See Example 5). The ELISA detects the purified Δ9 protein from the mammalian cells transiently transfected with Δ9 expression plasmid but not from the cells transiently transfected with empty expression plasmid.

Figure 16:
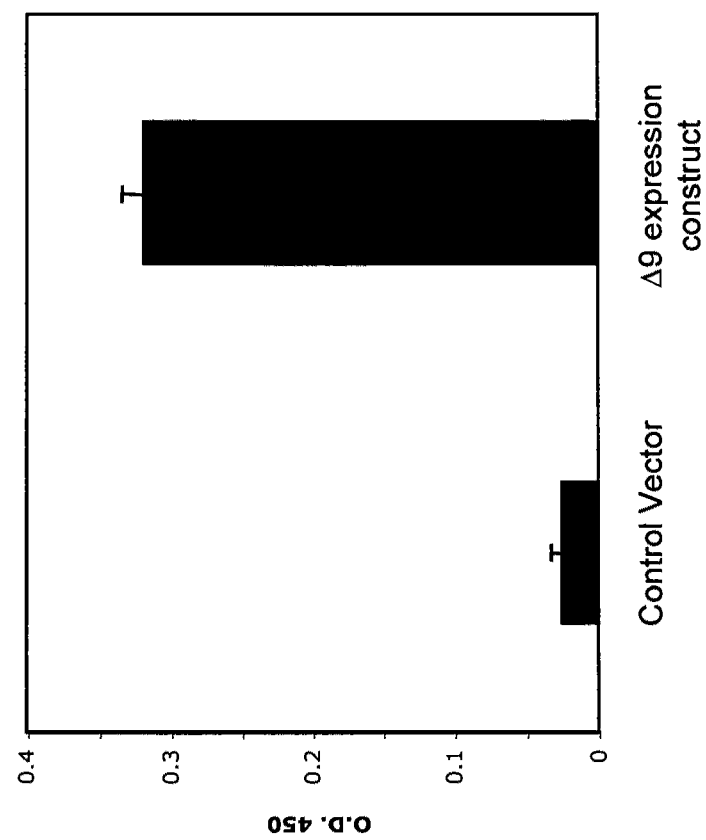
FIG. 16 depicts the validation of developed ELISA using recombinant Δ9 protein purified from the secreted source (i.e., culture medium from 293T).

FIG. 16 depicts the purified Δ9 protein from secreted source (culture medium) that was detected by the developed ELISA.

In both validation experiments (FIGS. 15 and 16), the results clearly show that the developed ELISA is capable to detect purified Δ9 protein.

Example 6

Detection of Δ9 in the 293T Culture Media

Figure 17:
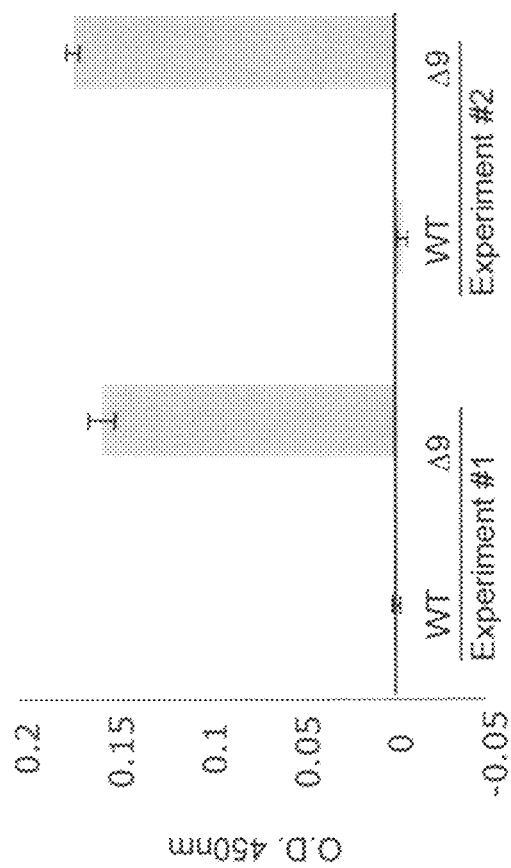
FIG. 17 depicts the ELISA experiment to detect the secreted Δ9 recombinant protein in the culture medium from the 293T cells transfected with the Δ9 expression plasmid. The result represents two (2) independent transfection experiments performed in the 293T cells.

Using the developed and validated ELISA, we proceeded to examine if the ELISA is capable to detect Δ9 in the cultured media (FIG. 17). In this series of study, mammalian 293T cells were transiently transfected with expression vectors carrying either wild-type IL-23Rα cDNA (WT) or Δ9 cDNA. The culture media were collected 48 hours post-transfection. Two independent transfection experiments were performed. No signal was detected in the 293T cell media transfected with the WT expression construct. However, signal was detected in the 293T cell media transfected with the Δ9 expression construct. The result clearly demonstrates that the ELISA is capable to detect the presence of Δ9 in the cultured media.

Example 7

EDTA-Treatment of Plasma a) Heparin-Plasma and Serum

Figure 18:
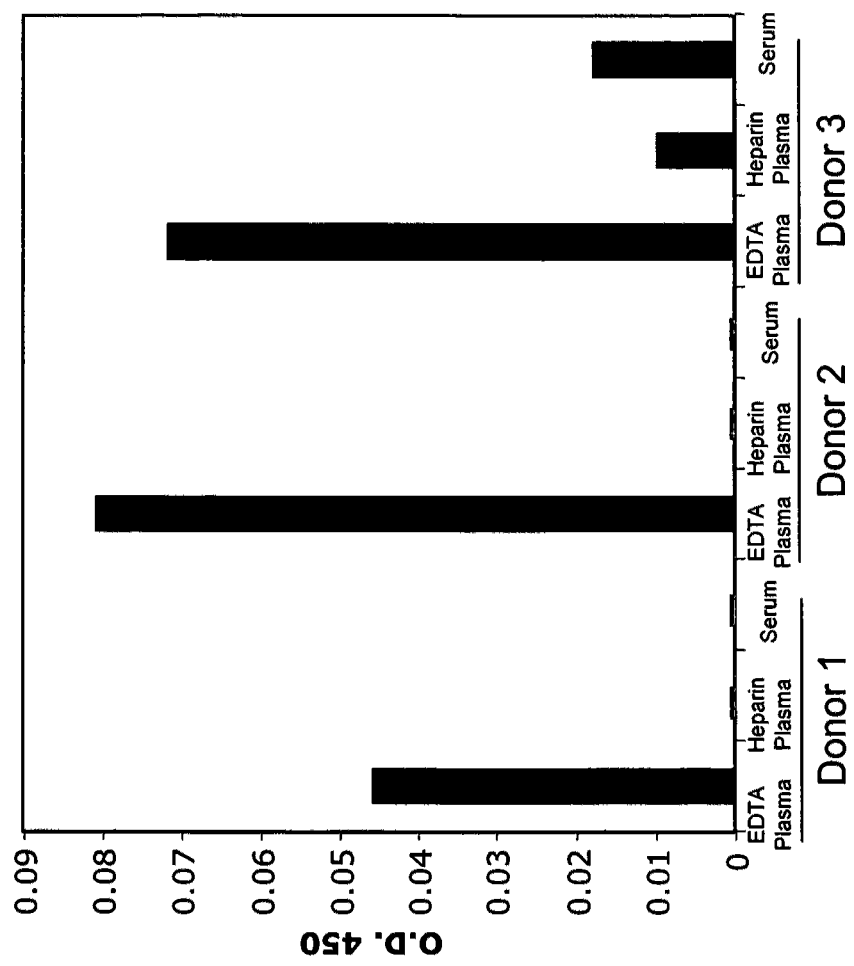
FIG. 18 depicts the use of ELISA to measure serological levels of Δ9 IL-23Rα in the sera or plasma from three (3) human donors. EDTA-plasma, heparin-plasma and serum were prepared from each donor.

We examined and compared different types of biological samples. They included EDTA-plasma, heparin-plasma and serum prepared from three (3) human subjects. FIG. 18 depicts the use of ELISA to measure serological levels of Δ9 IL-23Rα.

In the initial experiments using heparin-plasma, we observed some inconsistency in the detection of Δ9. In particular, Δ9 was detected in heparin-plasma only in donor #3, but not in donors #1 and #2 (FIG. 18). We also observed the similar inconsistency with sera from the three (3) donors (FIG. 18). It appeared that heparin-plasma and sera were not optimal as a biological sample.

EDTA-Plasma

Unlike heparin-plasma and serum, Δ9 IL-23R was detected consistently in all EDTA-plasma (FIG. 18). The finding was totally surprisingly. The results indicate that EDTA-plasma can provide good measurements for serological level of Δ9 IL-23R.

Example 8

Spike-Recovery and Dilution of Biological Samples a) Plasma Dilution

Figure 19:
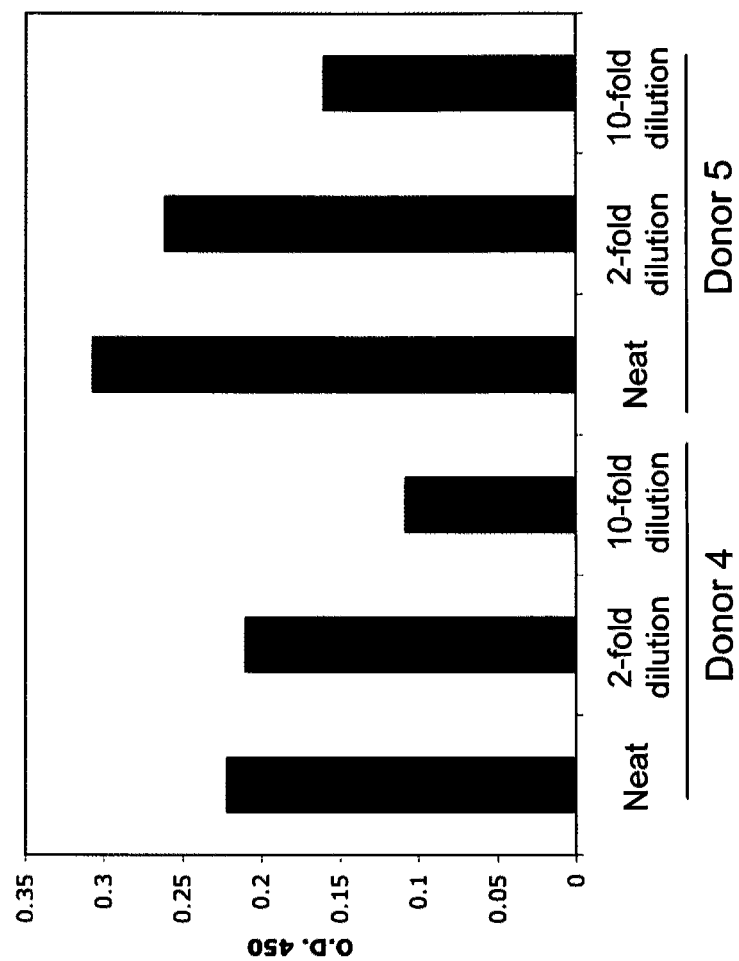
FIG. 19 depicts the EDTA plasma dilution study for ELISA. Experiment was performed using plasma samples from two (2) donors.

FIG. 19 depicts the plasma dilution study for ELISA. It has been reported that too much plasma used in the ELISA could result in inhibition. To optimize the amount of EDTA-plasma used in ELISA, neat, 2-fold dilution and 10-fold dilution of EDTA-plasma were prepared. EDTA plasma from two donors was used. In both donors, neat and 2-fold dilution of EDTA-plasma resulted in similar signal intensity in the ELISA test, suggesting that 2-fold dilution of EDTA-plasma is not enough. In addition, the neat EDTA-plasma has inhibitory effect in the ELISA. 10-fold dilution of EDTA-plasma resulted in a decrease in signal for around 50-60%, which is in the detectable range. Therefore, 10-fold dilution of plasma was used in our serological ELISA test.

Spike-Recovery: EDTA Plasma

Figure 20:
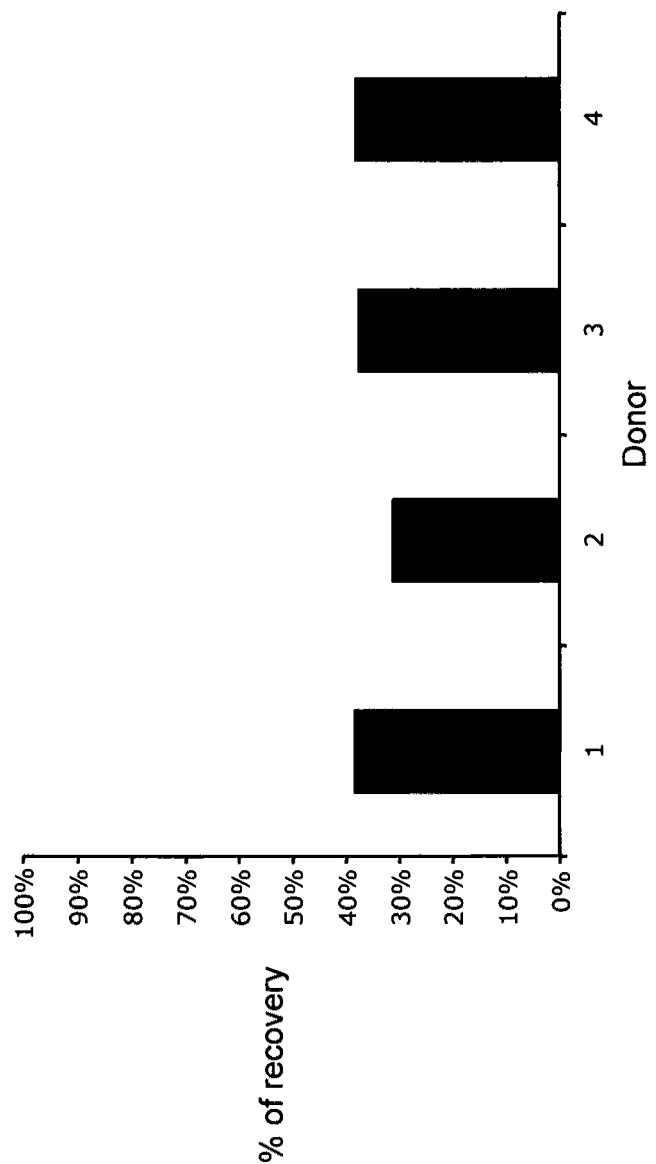
FIG. 20 depicts the spike and recovery experiment performed on the EDTA-plasma samples obtained from four (4) donors. 100 ng of IL-23R/Fc fusion protein was spiked into the plasma samples. Around 40% of IL-23R/Fc was recovered in the ELISA assay.

Spike and recovery experiment was performed on the EDTA-plasma samples obtained from 4 donors. 100 ng of IL-23R/Fc fusion protein was spiked into the 10-fold diluted plasma samples. Around 40% of IL-23R/Fc was recovered in the ELISA assay (FIG. 20).

c) Spike-Recovery: Synovial Fluid

Figure 21:
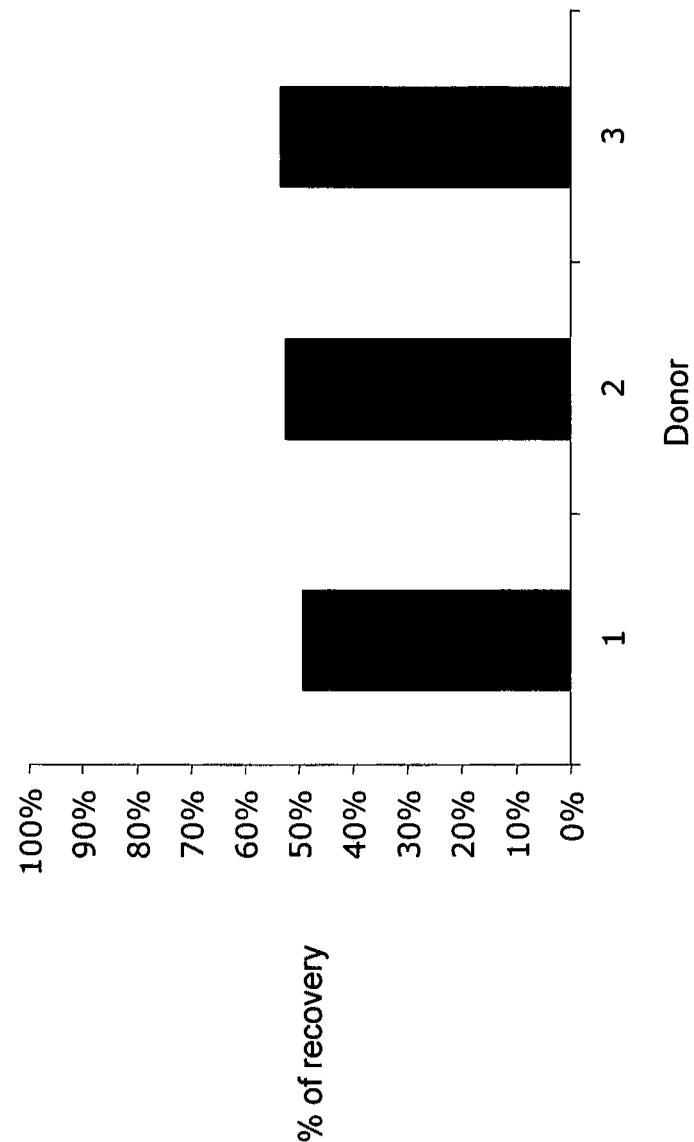
FIG. 21 depicts the spike and recovery experiment performed on the synovial fluids obtained from three (3) donors. 100 ng of IL-23R/Fc fusion protein was spiked into the fluids. Around 50% of IL-23R/Fc was recovered in the ELISA assay.

Spike and recovery experiment was performed on the synovial fluid samples obtained from 3 donors. 100 ng of IL-23R/Fc fusion protein was spiked into the 10-fold diluted plasma samples. Around 50% of IL-23R/Fc was recovered in the ELISA assay (FIG. 21).

d) Spike-Recovery: Cerebrospinal Fluid

Figure 22:
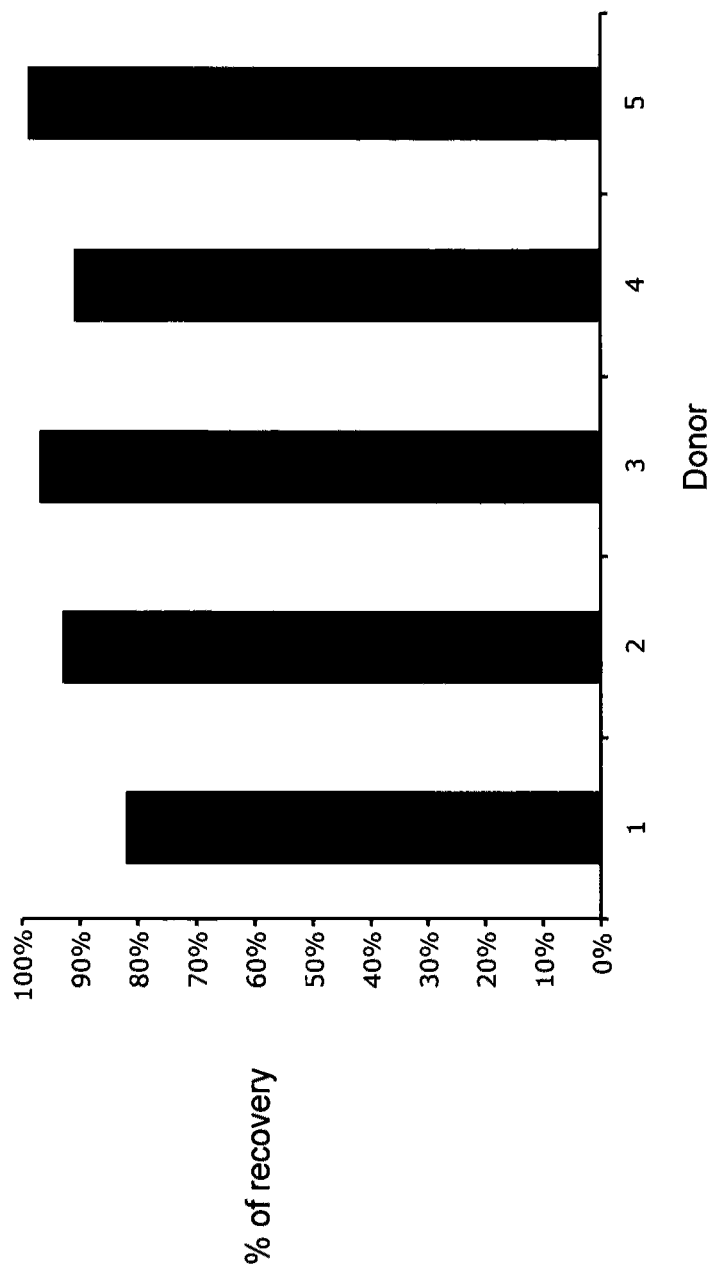
FIG. 22 depicts the spike and recovery experiment performed on the cerebrospinal fluids obtained from five (5) donors. 100 ng of IL-23R/Fc fusion protein was spiked into the fluids. More than 80% of IL-23R/Fc was recovered in the ELISA assay.

Spike and recovery experiment was performed on the cerebrospinal fluid samples obtained from 5 donors. 100 ng of IL-23R/Fc fusion protein was spiked into the 10-fold diluted plasma samples. More than 80% of IL-23R/Fc was recovered in the ELISA assay (FIG. 22).

e) Spike-Recovery: Amniotic Fluid

Figure 23:
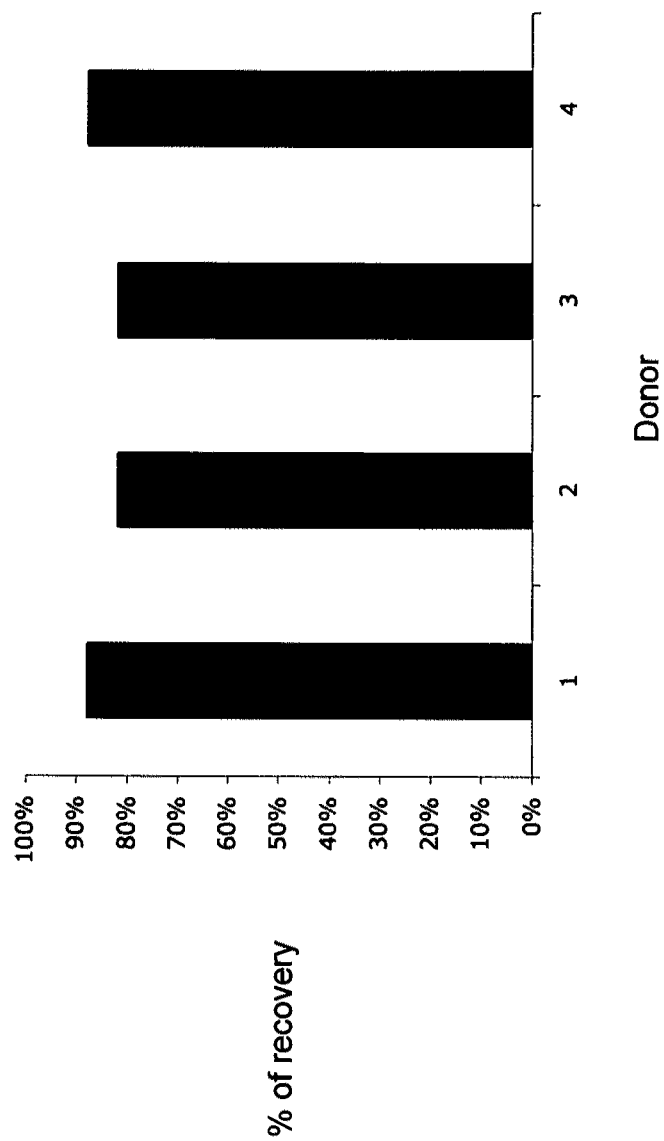
FIG. 23 depicts the spike and recovery experiment performed on the amniotic fluids obtained from four (4) donors. 100 ng of IL-23R/Fc fusion protein was spiked into the fluids. More than 80% of IL-23R/Fc was recovered in the ELISA assay.

Spike and recovery experiment was performed on the amniotic fluid samples obtained from 4 donors. 100 ng of IL-23R/Fc fusion protein was spiked into the 10-fold diluted plasma samples. More than 80% of IL-23R/Fc was recovered in the ELISA assay (FIG. 23).

Example 9

ELISA: Standard Curve

Figure 24:
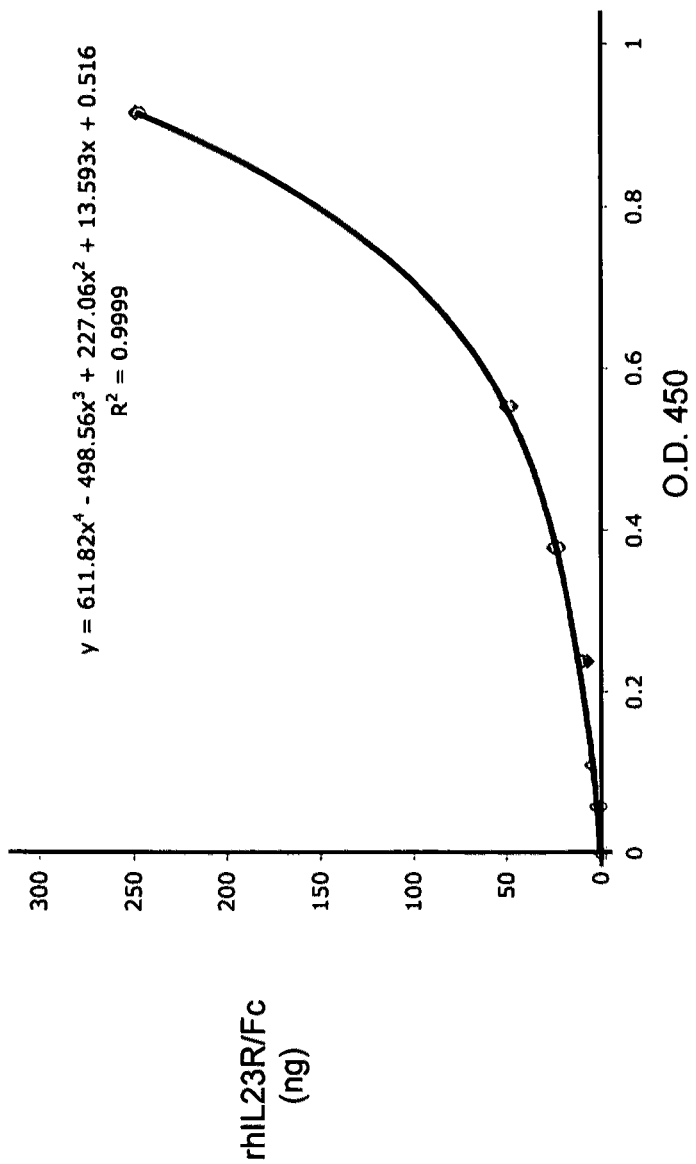
FIG. 24 depicts the standard curve generated using recombinant protein of human IL-23Rα, which is composed of extracellular domain of IL-23Rα and Fc region of IgG1. This standard curve was used to calculate the amount of naturally-occurring Δ9 protein in EDTA-plasma from O.D. 450 value.

In order to quantitated the serological levels of Δ9, standard curve was generated using recombinant protein of human IL-23Rα/Fc, which comprises an extracellular domain of IL-23R and Fc region of IgG1. This standard curve was used to calculate the amount of Δ9 IL-23Rα in EDTA-plasma from $OD_{450\ nm}$ value (FIG. 24).

Example 10

Figure 25:
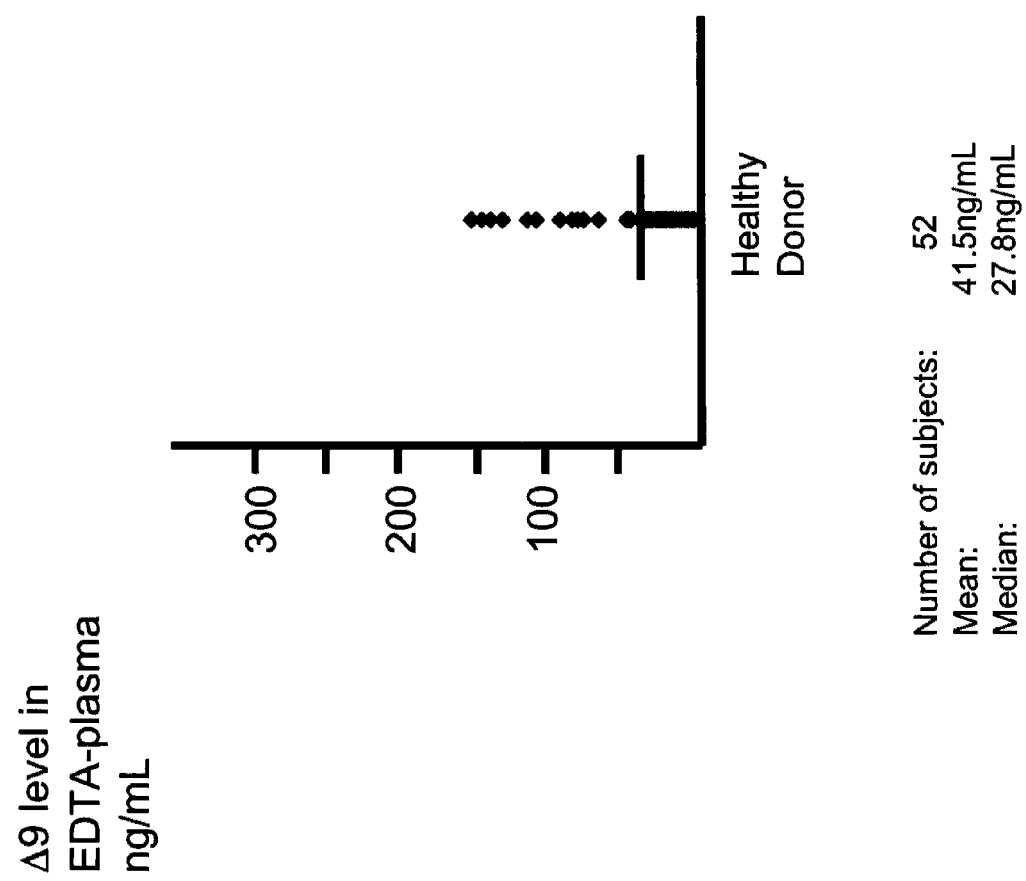
FIG. 25 depicts an ELISA experiment performed to detect the serological level of Δ9 in the plasma samples obtained from the healthy human donors with no known history of Crohn's disease. Totally, fifty-two (52) control plasma samples were analyzed. The mean and median Δ9 values were 41.5 ng/mL and 27.8 ng/mL, respectively.

Patient Study—Correlation of Increased Level of D9 and Crohn's Disease a) Control Human Subjects FIG. 25 depicts the correlation between serological levels of Δ9 IL-23Rα protein from fifty-two (52) human Healthy Donors (EDTA-plasma) with no known medical history of inflammatory, malignant or infectious bowel disease, including Crohn's disease. The mean and median of Δ9 IL-23Rα levels in this subject group were 41.5 ng/mL and 27.8 ng/mL, respectively.

b) Crohn's Disease Patients

Figure 26:
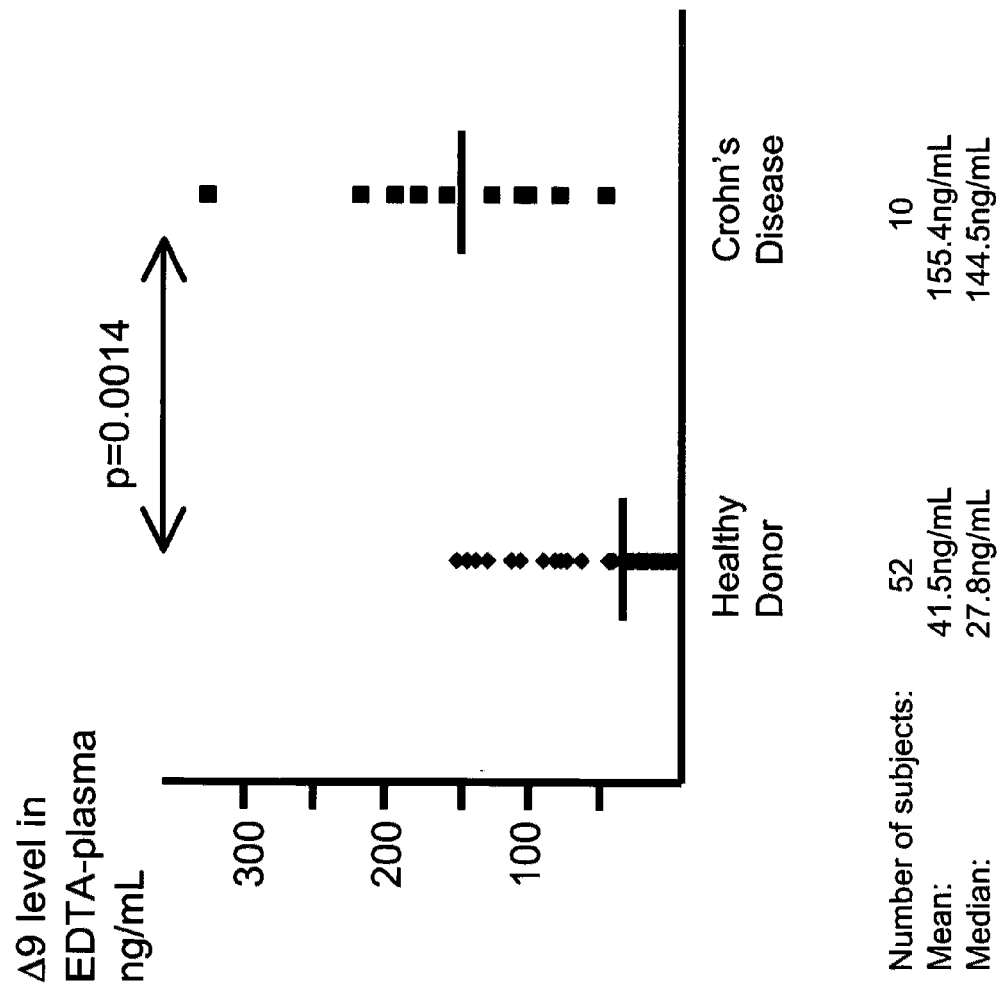
FIG. 26 depicts the ELISA experiment performed to detect the serological level of Δ9 protein in the EDTA-plasma samples obtained from the human donors with a medical history of Crohn's disease. The mean and median values of Δ9 IL-23Rα level were 155.4 ng/mL and 144.5 ng/mL, respectively. Both mean and median in Crohn's patients were higher than those in the normal group. The difference between the two groups was statistically significant ($p=0.0014$; Student's t-test, two-tailed).

FIG. 26 depicts the serological levels of Δ9 IL-23Rα in ten (10) human subjects with a medical history of Crohn's disease. The mean and median of Δ9 IL-23Rα levels in the Crohn's disease patient group were 155.4 ngmL and 144.5 ng/mL, respectively. Note that the serological levels of Δ9 IL-23Rα in the Crohn's disease patients, when compared to that Healthy Donor group described in FIG. 25 (Example 10.a) exhibited higher values. The difference between the two groups was statistically significant (p=0.0014, Student's t-test, two-tailed).

Example 11

Figure 27:
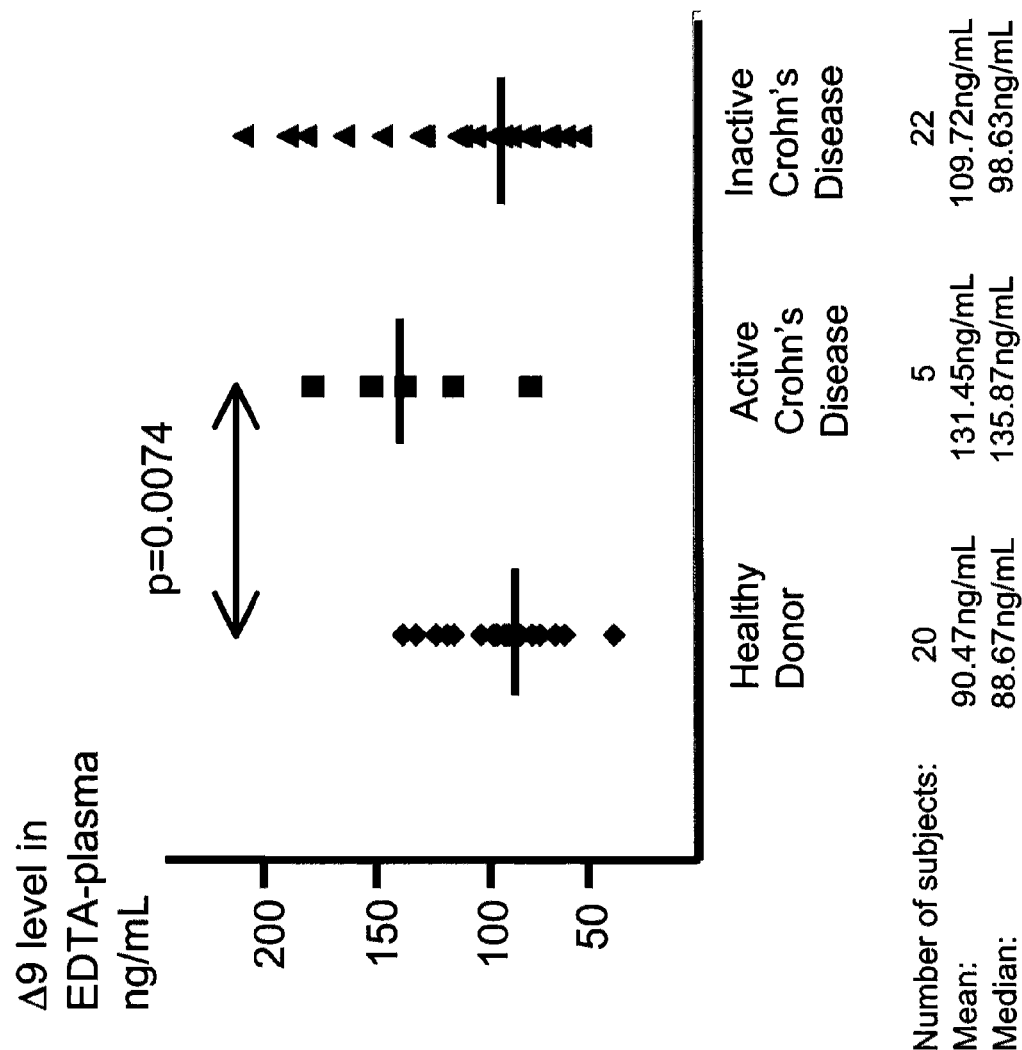
FIG. 27 depicts the ELISA experiment performed to detect the serological levels of Δ9 protein the EDTA-plasma samples obtained from patients with active Crohn's disease. The mean and median values of Δ9 protein in the EDTA-plasma were 131.45 ng/mL and 135.87 ng/mL, respectively. Both mean and median values of Δ9 protein in active Crohn's disease patients were higher than those in the control group (mean: 90.47 ng/mL; median: 88.67 ng/mL). The difference between the two groups was statistically significant ($p=0.0074$; Student's t-test, two-tailed). The mean and median values of Δ9 protein in the EDTA-plasma of the inactive Crohn's disease patients were 109.72 ng/mL and 98.63 ng/mL, respectively.

Patient Study—Correlation of Increased Level of Δ9 IL-23Rα with the Presence of Active Crohn's Disease Patients FIG. 27 depicts the correlation between serological levels of Δ9 IL-23Rα and patients who suffer from an active Crohn's disease at the time of the study. In this study, we examined a separate independent group (n=22) of Healthy Donors as well as a separate independent group of patients who suffered from active Crohn's disease (n=5). The mean and median of Δ9 IL-23Rα levels in the control Healthy Donors were 90.47 ng/ml and 88.67 ng/mL, respectively. The mean and median of Δ9 IL-23Rα levels in the active Crohn's disease patient group were 131.45 ng/mL and 135.87 ng/mL, respectively. Note that the Δ9 IL-23Rα levels were found to be significantly higher in the active Crohn's disease patients. The difference between the two groups was statistically significant (p=0.0074, Student's t-test, two-tailed).

We also examined, in a parallel study, the correlation between serological levels of Δ9 IL-23Rα and patients who had a prior history of Crohn's disease, but were symptom-free at the time of the study (which we called inactive Crohn's disease group; n=22). The mean and median of Δ9 IL-23Rα levels in the inactive Crohn's disease patient group were 109.72 ng/mL and 98.63 ng/mL, respectively. One possible explanation for this observation may relate to the possibility that the levels of Δ9 IL-23Rα subsided incompletely in some patient in this group.

Example 12

Patient Study—Correlation of Increased Level of Δ9 IL-23Rα with a History of Colonic Resection in Inactive Crohn's Disease Patients In this study, we further examined a different basis for the observed levels of Δ9 IL-23Rα in the inactive Crohn's patients. We noted that the entire inactive Crohn's patients could be further divided into two (2) groups; namely, (i) with an intestinal resection procedure, or (ii) without an intestinal resection procedure. Of the 22 inactive Crohn's disease patients, 19 patients had medical history concerning intestinal resection. Out of these 19 patients, nine (9) patients had previously received an intestinal resection, while ten (10) patients had never received such a procedure.

The mean and median values of Δ9 protein in the EDTA-plasma of resection patients were 141.57 ng/mL and 139.49 ng/mL, respectively. The mean and median values of Δ9 protein in the EDTA-plasma of non-resection patients were 75.40 ng/mL and 77.98 ng/mL, respectively. The Δ9 protein in resection patients was higher than that in the non-resection patients. The difference between the two groups was statistically significant (p=0.009; Student's t-test, two-tailed).

Example 13

Figure 28:
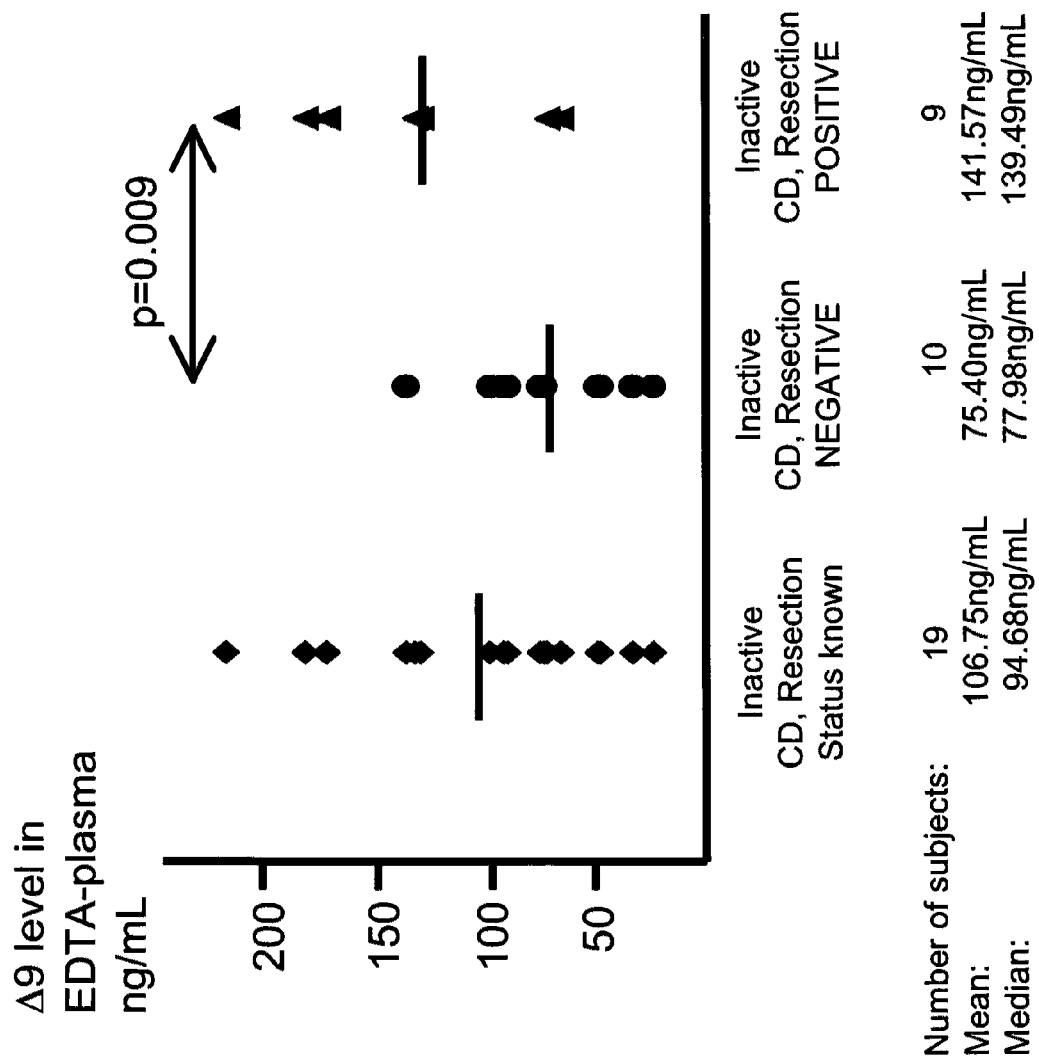
FIG. 28 depicts the ELISA experiment performed to detect the serological levels of Δ9 protein in the EDTA-plasma samples obtained from patients with inactive Crohn's disease with or without resection of an intestinal tract (i.e., part of the intestine was removed). The mean and median values of Δ9 protein in the EDTA-plasma of resection patients were 141.57 ng/mL and 139.49 ng/mL, respectively. The mean and median values of Δ9 protein in the EDTA-plasma of non-resection patients were 75.40 ng/mL and 77.98 ng/mL, respectively. Note that the Δ9 protein in resection group is significantly higher than those in non-resection patients. The difference between the two groups was statistically significant ($p=0.009$; Student's t-test, two-tailed).

Pregnancy Study—Correlation of Decreased Levels of Δ9 IL-23Rα with Human Pregnancy FIG. 28 depicts the serological detection of Δ9 IL-23Rα levels in the circulation of two groups of women. Fifteen (15) healthy non-pregnant women between the ages of 18 and 55, and forty-two (42) otherwise healthy, pregnant women of not more than eleven (11) weeks gestation had Δ9 IL-23Rα levels determined. The Δ9 IL-23Rα mean and median levels detected in the pregnant women were 41.5 ng/mL and 27.8 ng/mL, respectively. The Δ9 IL-23Rα mean and median levels detected in the non-pregnant women were 100.6 ng/mL and 92.5 ng/mL, respectively. The Δ9 IL-23Rα level in non-pregnant women was higher than that in pregnant women. The difference between the two groups was statistically significant (p<0.0001; Student's t-test, two tailed).

Example 14

Figure 29:
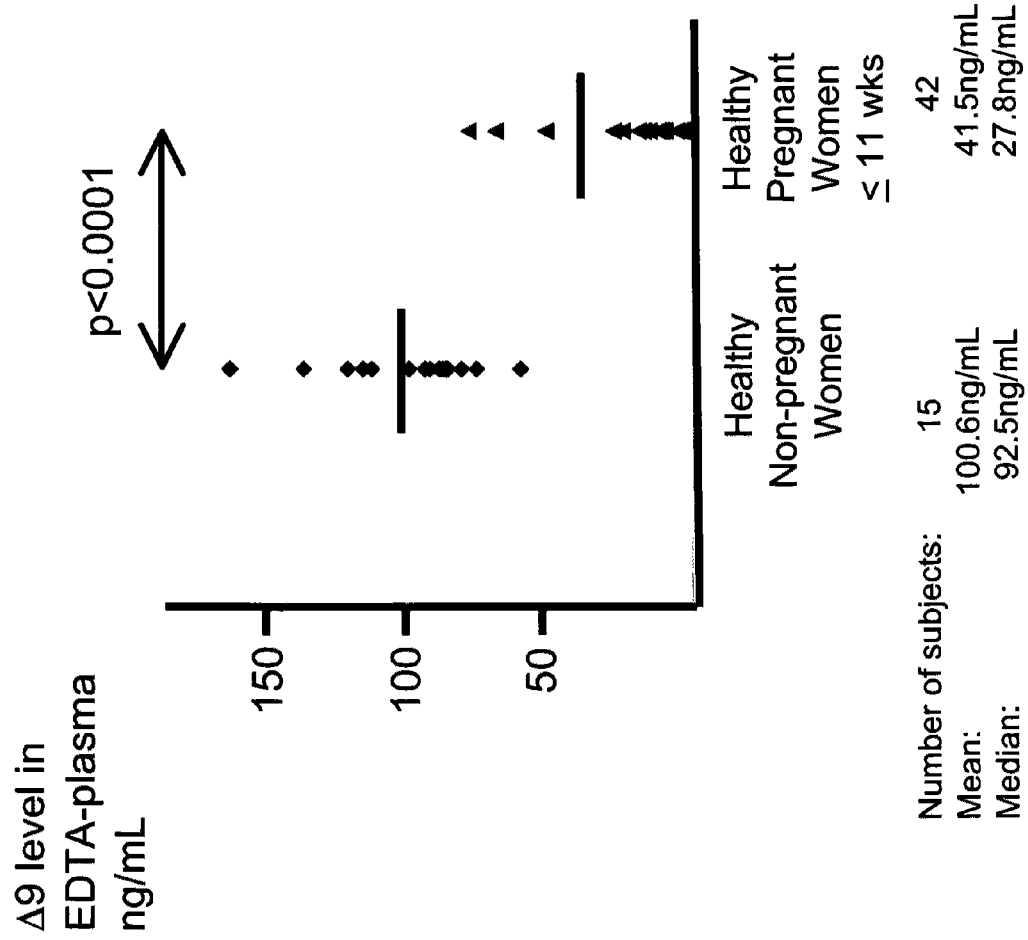
FIG. 29 depicts the ELISA experiment performed to detect the serological levels of Δ9 protein in the EDTA-plasma samples obtained from non-pregnant women and pregnant women (with not more than eleven (11) weeks gestation). The mean and median values of Δ9 protein in the pregnant women were 41.5 ng/mL and 27.8 ng/mL, respectively. The mean and median values of Δ9 protein in the control non-pregnant women were 100.6 ng/mL and 92.5 ng/mL, respectively. The Δ9 protein levels in the non-pregnant women were found to be higher than those in the pregnant women, and the difference between the two groups was statistically significant ($p<0.0001$; Student's t-test, two-tailed).

Pregnancy Study—Correlation of Levels of Δ9 IL-23Rα with Length of Pregnancy a) Δ9 IL-23Rα Levels in Circulating Plasma FIG. 29 depicts the serological detection of Δ9 IL-23Rα levels in the circulation of pregnant women. Seventy-three (73) women with healthy, normal pregnancies had Δ9 IL-23Rα levels determined at various times between week seven and week thirty-six. The levels detected up to and including week 20 (n=47) were higher (mean, 14.76 ng/mL; median 4.19 ng/mL) than those detected after week 20 (n=27; mean 3.17 ng/mL; median 2.68 ng/mL). The difference between the two groups was statistically significant (p<0.004; Student's t-test, two tailed). Note that the "week 20" was chosen because miscarriage (i.e., loss of pregnancy) occurs at or before the $20^{th}$ week of pregnancy (according to the American Congress of Obstetricians and Gynecologists).

Δ9 IL-23Rα Levels in Amniotic Fluid

Figure 30:
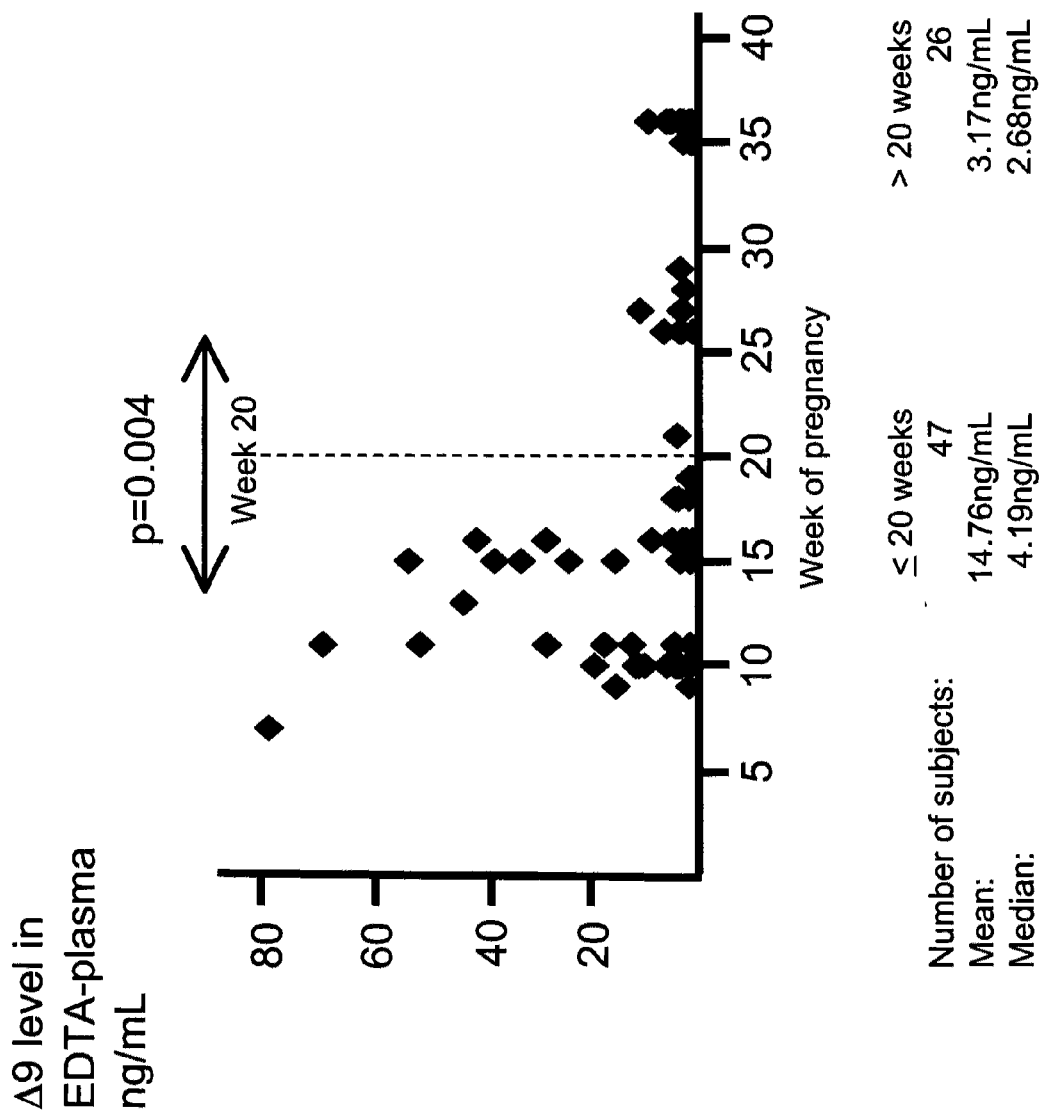
FIG. 30 depicts the ELISA experiment performed to detect the serological level of Δ9 protein in the EDTA-plasma samples obtained from pregnant women. The serological level of Δ9 protein is plotted according to weeks of gestation. Pregnant women of greater than twenty (20) weeks gestation (i.e., mean: 3.17 ng/mL, median: 2.68 ng/mL) had lower levels when compared to those of twenty (20) weeks or less (i.e., mean: 14.76 ng/mL, median: 4.19 ng/mL). The difference between the two groups was statistically significant (p<0.004; Student's t-test, two-tailed).
Figure 31:
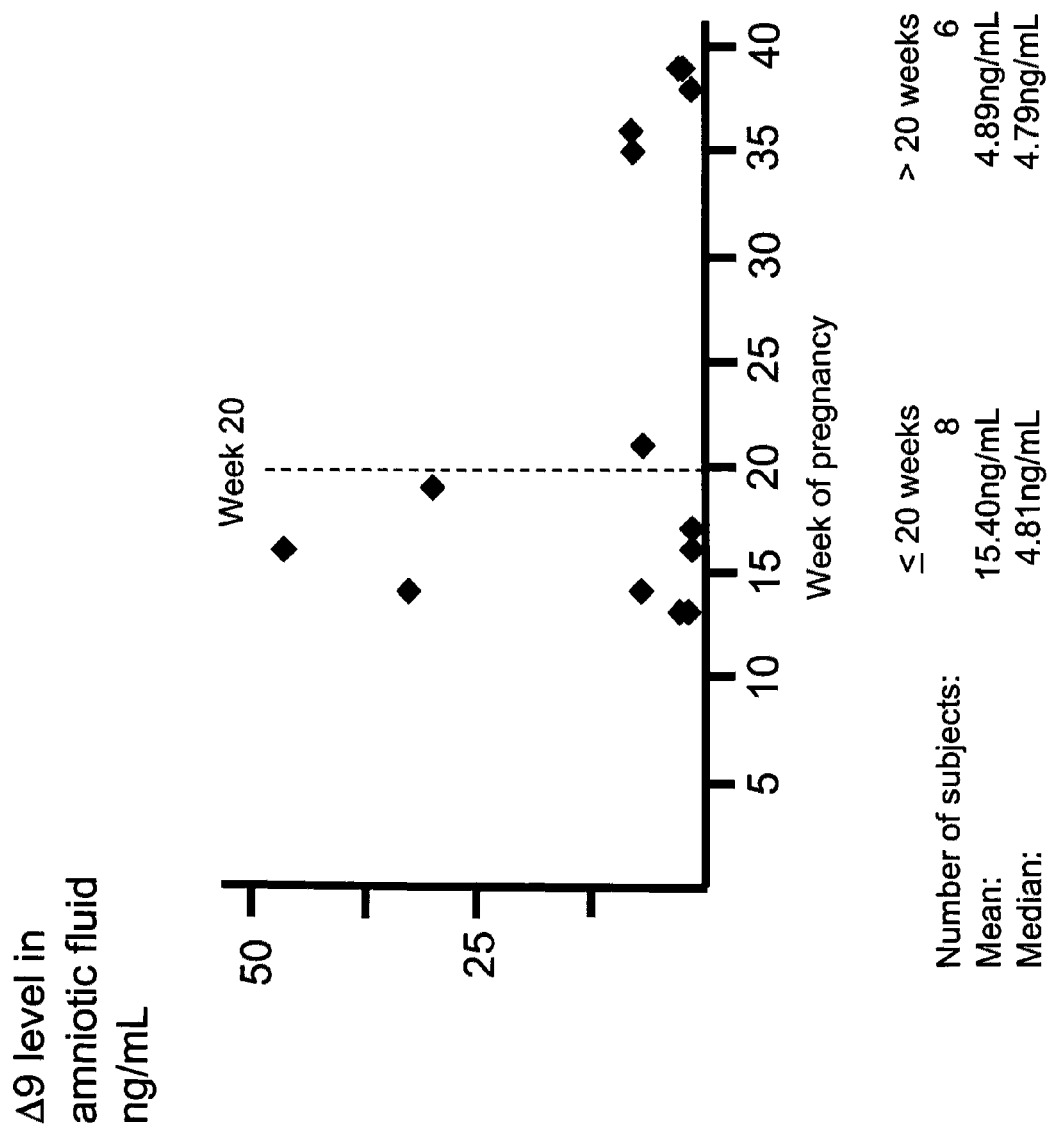
FIG. 31 depicts the ELISA experiment performed to detect the serological level of Δ9 protein in amniotic fluid samples obtained from pregnant women. The serological level of Δ9 protein is plotted according to weeks of gestation. Pregnant women of greater than twenty (20) weeks gestation (i.e., mean: 4.89 ng/mL, median: 4.79 ng/mL) had lower levels than those of twenty (20) weeks or less (i.e., mean: 15.40 ng/mL, median: 4.18 ng/mL).

FIG. 30 depicts the serological detection of Δ9 IL-23Rα levels in amniotic fluid during pregnancy. Amniotic fluid from fourteen (14) women with healthy, normal pregnancies had Δ9 IL-23Rα levels determined at various times between week twelve and week thirty-eight. The Δ9 IL-23Rα levels detected up to and including week 20 (n=8) were higher (mean, 15.40 ng/mL; median, 4.81 ng/mL) than those detected after week 20 (n=6; mean, 4.89 ng/mL; median, 4.79 ng/mL). Thus, circulating levels of Δ9 IL-23Rα (FIG. 29) reflect those in the amniotic fluid (FIG. 30), allowing monitoring of the intra-uterine levels of Δ9 IL-23Rα without an invasive procedure such as amniocentesis. Note that the profile of Δ9 IL-23Rα in amniotic fluid parallels to that of plasma, albeit with a slight time delay. Accordingly, it is believed that detecting changes in Δ9 IL-23Rα levels in plasma can accurately predict changes in the levels of Δ9 IL-23Rα levels in amniotic fluid. Because the amniotic fluid bathes the fetus, we obtained direct evidence that Δ9 IL-23Rα is present in the amniotic fluid (connecting maternal and fetus). We speculate the Δ9 IL-23Rα may play a role in establishing such important connection between mother and fetus.

Materials and Methods

Construction of Expression Constructs

Human wild-type IL-23Rα was amplified from human peripheral blood mononuclear cells (PBMC)'s cDNA using the following primer pair by Pfx high fidelity DNA polymerase (Invitrogen).

```
P1 F:
                                         (SEQ ID NO: 5)
CAGGTTGAAAGAGGGAAACAGTCT

C-Flag R:
                                         (SEQ ID NO: 6)
CTCGAGCTACTTGTCATCGTCGTCCTTGTAAT

CCTTTTCCAAGAGTGAAATCCTAATG
```

The amplified PCR products were run on agarose gels and purified using DNA gel purification kit from Qiagen. The gel purified PCR products were cloned into pCDNA3.3 using TOPO TA cloning kit from Invitrogen. The ligated products were transformed into Top10 competent cell (Invitrogen).

The transformed competent cells were selected using LB plate containing ampicillin for 16 hours at 37° C. The ampicillin resistant clones were cultured in 2 mL of LB medium with ampicillin for 16 hours at 37° C. DNA was extracted from the bacteria culture using DNA mini-preparation kit from Qiagene.

The DNA was then validated by restriction enzyme digestion and sequencing. The confirmed expression construct was used to prepare high quality DNA for transfection using DNA maxi-preparation kit from Qiagene. The purified DNA was quantified by Nano-drop (Thermo Scientific).

The expression constructs of pΔ11, Δ8, Δ9 and Δ8,9 were made by the same approach except using different primer sets.

Generation of Expression Constructs

Expression construct of wild-type IL-23R (WT) was generated by PCR using Pfx DNA polymerase (Invitrogen). Forward primer (5' ATGAATCAGGTCACATTCAATG 3') (SEQ ID NO: 12) and reverse primer (5' CTACTTGTCATCGTCGTCCTTGTAATCCTTTTCCAAGAGTGAAATCCTATTG 3') (SEQ ID NO: 13) were used to amplify wild-type IL-23R from PBMCs cDNA. The amplified PCR product was treated with Taq polymerase to add 3'-A overhang to each end of PCR. The gel-purified product was then subcloning into mammalian expression plasmid using the pcDNA3.3 TOPO TA Cloning kit from Invitrogen. The correct expression construct was subjected to validation by sequencing.

Constructions of pΔ11, Δ9 and Δ89 expression plasmids were performed using the same method except pcDNA3.3 IL-23R WT was used as PCR template. Difference primer sets were also used as shown in the following:

```
pΔ11
Forward primer:
                                       (SEQ ID NO: 14)
5' ATGAATCAGGTCACATTCAATG 3'

Reverse primer:
                                       (SEQ ID NO: 15)
5' CTACTTGTCATCGTCGTCCTTGTAATCTCTCTGTAGCATT

TTCACAACATTGCT 3'

Δ9
Forward primer:
                                       (SEQ ID NO: 16)
5' ATGAATCAGGTCACATTCAATG 3'

Reverse primer:
                                       (SEQ ID NO: 17)
5' CTACTTGTCATCGTCGTCCTTGTAATCACA

ATA AGATCCTTCTTTTAATCCAGAAGTAAGGTGC 3'

Δ8, 9
Forward primer:
                                       (SEQ ID NO: 18)
5' ATGAATCAGGTCACATTCAATG 3'

Reverse primer:
                                       (SEQ ID NO: 19)
5' CTACTTGTCATCGTCGTCCTTGTAATCACA

ATA AGATCCTTCTTTTAATCCTGTTTCAGGTGTT 3'
```

Construction of Δ8 expression plasmid was performed by PCR overlap extension. Two fragments, fragment 1: Translation start to Exon 7 and fragment 2: Exon 9 to Translation stop, were amplified using the following primer pairs.

```
Fragment 1
Forward primer:
                                       (SEQ ID NO: 20)
5' ATGAATCAGGTCACATTCAATG 3'

Reverse primer:
                                       (SEQ ID NO: 21)
5' CTGTTTCAGGTGTT 3'

Fragment 2
Forward primer:
                                       (SEQ ID NO: 22)
5' AACACCTGAAACAG 3'

Reverse primer:
                                       (SEQ ID NO: 23)
5' CTACTTGTCATCGTCGTCCTTGTAATCCTTTTCCAAGAGT

GAAATCCTATTG 3'
```

Two amplified fragments (1 and 2) were then joined together by overlap extension. The final combined fragment was subcloned into pcDNA3.3 TOPO expression vector.

Western Blotting Analysis

Cells were collected, washed in PBS and lysed in ProteoJET mammalian cell lysis reagent (Fermentas) with protease and phosphatase inhibitors (Sigma). Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (Bio-Rad) per manufacturer's recommendations. Membranes were blocked in 5% milk/TPBT at room temperature for 1 hour. Membranes were first probed with antibodies against p-STAT1, p-STAT2, p-STAT3 or p-STAT5 (cell signaling technology), and then stripped and reprobed for STAT1, STAT2, STAT3 or STAT5 (cell signaling technology).

Transfection of 293T Cells

One day before the transient transfection experiment, 293T cells were trypsinized and cultured on the 10-cm culture plate. The cell density was maintained at around 60-80% confluence at the time of transfection. 10 μg of DNA was mixed with 500 μl of OptiMEM (Invitrogen). 40 μl of FuGene HD transfection reagent (Roche) was diluted in 500 μl of OptiMEM. The diluted transfection reagent was then added to DNA mix and vortex for two seconds to mix the contents. The mixture was incubated at room temperature for 15 minutes before addition to the 293T cells. Both culture media and cell lysates were prepared after 36-48 hours post-transfection for purification of Δ9 IL-23Rα.

Purification of Intracellular Δ9 IL-23Rα

Cells were collected, washed in PBS and lysed in ProteoJET mammalian cell lysis reagent (Fermentas) with protease and phosphatase inhibitors (Sigma). Lysates were centrifuged and supernatants were prepared for purification. C-terminal flag-tagged Δ9 was immuno-precipitated from cellular lysates using anti-flag M2 affinity gel (Sigma) according to the manufacturer's instructions. The precipitated Δ9 was eluted by excessive Flag peptide (Sigma). The quality and quantity of the purified Δ9 IL-23Rα were measured by PAGE gels (Bio-Rad) and stained with Coomassie Blue (Bio-Rad).

Purification of Δ9 IL-23Rα from Culture Medium

The purification of Δ9 from culture medium was the same as that of the intracellular Δ9, except the concentrated cultured media were used. Expression construct of Δ9 was transiently transfected into 293T cells by Fugene HD transfection reagent (Roche applied science). The culture medium from the transfected cells was collected and then concentrated using Amicon ultra centrifugal filter 30K (Millipore). C-terminal flag-tagged Δ9 was immuno-precipitated from the concentrated medium using anti-flag M2 affinity gel (Sigma) according to the manufacturer's instructions. The precipitated Δ9 was eluted by excessive Flag peptide (Sigma). The quality and quantity of purified Δ9 were measured by PAGE gels (Bio-rad) stained with Coomassie Blue (Bio-rad). The purification steps of Δ9 include:

(1) Transfecting Δ9 expression construct into 293T cells;
(2) Collecting culture media after 48 hours, 72 hours or 96 hours post-transfection;
(3) Centrifugating to remove dead cells and unattached cells;
(4) Concentrating culture media using Amicon Ultra-15 Centrifugal Filter with 30 kDa cutoff;
(5) Immuno-precipitating Δ9 by anti-Flag M2 Affinity Gel;
(6) Eluting Δ9 by excessive Flag peptides; and
(7) Measuring the quantity and purity of purified Δ9 by gel electrophoresis and Commassie Blue staining.

Immunoblot Assay (Western Blotting)

Cells were collected, washed in PBS and lysed in ProteoJET mammalian cell lysis reagent (Fermentas) with protease and phosphatase inhibitors (Sigma). Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (Bio-Rad) per manufacturer's recommendations. Membranes were blocked in 5% milk/TPBT at room temperature for 1 hour. Membranes were probed with anti-flag (sigma), mouse anti-hIL-23Rα (R&D) and biotinlyated goat anti-hIL-23Rα (R&D).

Enzyme-Linked Immunosorbent Assay (ELISA)

Sandwich ELISA was developed using 5 μg/ml of mouse anti-hIL-23Rα (R&D) as capture antibody and 1.6 μg/ml of Goat biotinlyated anti-hIL-23Rα (R&D) as detection antibody. Capture antibody was first coated on the microtiter plate using 50 mM of bicarbonate buffer (pH=9.6) at 4° C. overnight. The plate was then blocked with 10% FBS/TBST at room temperature for 2 hours. Samples were added to the well and incubated at 4° C. overnight. Detection antibody in TBST was added to the wells and incubated at room temperature for 2 hours. The plate was extensively washed with TBST during each change. The immuno-complex was detected by addition of Streptavidin-HRP (R&D) and TMB substrate (eBioscience). The plate was read at $OD_{450\ nm}$.

While the present invention has been described in connection with specific embodiments thereof, it will be understood that it is capable of further modifications and this application is intended to cover any variations of the invention thereof. One of skill in the art will recognize that various modifications may be made to the embodiments described herein without departing from the spirit and scope of the invention, which is defined by the appended claims. All the references and patents cited in this application are incorporated by reference in their entirety.

REFERENCES

1. Oppmann B, Lesley R, Blom B, Timans J C, Xu Y, Hunte B, Vega F, Yu N, Wang J, Singh K, Zonin F, Vaisberg E, Churakova T, Liu M, Gorman D, Wagner J, Zurawski S, Liu Y, Abrams J S, Moore K W, Rennick D, de Waal-Malefyt R, Hannum C, Bazan J F, Kastelein R A. Novel p19 protein engages IL-12p40 to form a cytokine, IL-23, with biological activities similar as well as distinct from IL-12. Immunity. 2000 November; 13(5):715-25.
2. Parham C, Chirica M, Timans J, Vaisberg E, Travis M, Cheung J, Pflanz S, Zhang R, Singh K P, Vega F, To W, Wagner J, O'Farrell A M, McClanahan T, Zurawski S, Hannum C, Gorman D, Rennick D M, Kastelein R A, de Waal Malefyt R, Moore K W. A receptor for the heterodimeric cytokine IL-23 is composed of IL-12Rbeta1 and a novel cytokine receptor subunit, IL-23R. J Immunol. 2002 Jun. 1; 168(11):5699-708.
3. Kan S H, Mancini G, Gallagher G. Identification and characterization of multiple splice forms of the human interleukin-23 receptor alpha chain in mitogen-activated leukocytes. Genes Immun. 2008 October; 9(7):631-9. Epub 2008 Aug. 28
4. Mancini G, Kan S H, Gallagher G. A novel insertion variant of the human IL-23 receptor-alpha chain transcript. Genes Immun. 2008 September; 9(6):566-9. Epub 2008 Jul. 10.
5. Aggarwal S, Ghilardi N, Xie M H, de Sauvage F J, Gurney A L. Interleukin-23 promotes a distinct CD4 T cell activation state characterized by the production of interleukin-17. J Biol Chem. 2003 Jan. 17; 278(3):1910-4. Epub 2002 Nov. 3.
6. Murphy C A, Langrish C L, Chen Y, Blumenschein W, McClanahan T, Kastelein R A, Sedgwick J D, Cua D J. Divergent pro- and antiinflammatory roles for IL-23 and IL-12 in joint autoimmune inflammation. J Exp Med. 2003 Dec. 15; 198(12):1951-7. Epub 2003 Dec. 8.
7. Cua D J, Sherlock J, Chen Y, Murphy C A, Joyce B, Seymour B, Lucian L, To W, Kwan S, Churakova T, Zurawski S, Wiekowski M, Lira S A, Gorman D, Kastelein R A, Sedgwick J D. Interleukin-23 rather than interleukin-12 is the critical cytokine for autoimmune inflammation of the brain. Nature. 2003 Feb. 13; 421(6924): 744-8.
8. Elson C O, Cong Y, Weaver C T, Schoeb T R, McClanahan T K, Fick R B, Kastelein R A. Monoclonal anti-interleukin 23 reverses active colitis in a T cell-mediated model in mice. Gastroenterology. 2007 June; 132(7): 2359-70. Epub 2007 Apr. 13.
9. Wong C K, Lit L C, Tam L S, Li E K, Wong P T, Lam C W. Hyperproduction of IL-23 and IL-17 in patients with systemic lupus erythematosus: implications for Th17-mediated inflammation in auto-immunity. Clin Immunol. 2008 June; 127(3):385-93. Epub 2008 Mar. 25.
10. Yu R Y, Gallagher G. A naturally occurring, soluble antagonist of human IL-23 inhibits the development and in vitro function of human Th17 cells. J Immunol. 2010 Dec. 15; 185(12):7302-8. Epub 2010 Nov. 12.
11. Murphy K M, Reiner S L. The lineage decisions of helper T cells Nat Rev Immunol. 2002 December; 2(12): 933-44. Review.
12. Harrington L E, Hatton R D, Mangan P R, Turner H, Murphy T L, Murphy K M, Weaver C T. Interleukin 17-producing CD4+ effector T cells develop via a lineage distinct from the T helper type 1 and 2 lineages. Nat Immunol. 2005 November; 6(11):1123-32. Epub 2005 Oct. 2.
13. Langrish C L, Chen Y, Blumenschein W M, Mattson J, Basham B, Sedgwick J D, McClanahan T, Kastelein R A, Cua D J. IL-23 drives a pathogenic T cell population that induces autoimmune inflammation. J Exp Med. 2005 Jan. 17; 201(2):233-40.
14. Harrington L E, Mangan P R, Weaver C T. Expanding the effector CD4 T-cell repertoire: the Th17 lineage. Curr Opin Immunol. 2006 June; 18(3):349-56. Epub 2006 Apr. 17. Review.

15. Korn T, Oukka M, Kuchroo V, Bettelli E. Th17 cells: effector T cells with inflammatory properties. Semin Immunol. 2007 December; 19(6):362-71. Epub 2007 Nov. 26. Review.
16. Ouyang W, Kolls J K, Zheng Y. The biological functions of T helper 17 cell effector cytokines in inflammation. Immunity. 2008 April; 28(4):454-67. Review.
17. Louten J, Boniface K, de Waal Malefyt R. Development and function of TH17 cells in health and disease. J Allergy Clin Immunol. 2009 May; 123(5):1004-11. Review.
18. Abraham C, Cho J. Interleukin-23/Th17 pathways and inflammatory bowel disease. Inflamm Bowel Dis. 2009 July; 15(7):1090-100. Review.
19. Zhang J H, He H, Borzychowski A M, Takeda K, Akira S, Croy B A. Analysis of cytokine regulators inducing interferon production by mouse uterine natural killer cells. Biol Reprod. 2003 August; 69(2):404-11. Epub 2003 Mar. 19.
20. Uz Y H, Murk W, Yetkin C E, Kayisli U A, Arici A. Expression and role of interleukin-23 in human endometrium throughout the menstrual cycle and early pregnancy. J Reprod Immunol. 2010 December; 87(1-2):21-7. Epub 2010 Aug. 10.
21. Nakashima A, Ito M, Yoneda S, Shiozaki A, Hidaka T, Saito S. Circulating and decidual Th17 cell levels in healthy pregnancy. Am J Reprod Immunol. 2010 February; 63(2):104-9. Epub 2009 Dec. 15.
22. Wang W J, Hao C F, Yi-Lin, Yin G J, Bao S H, Qiu L H, Lin Q D. Increased prevalence of T helper 17 (Th17) cells in peripheral blood and decidua in unexplained recurrent spontaneous abortion patients. J Reprod Immunol. 2010 March; 84(2):164-70. Epub 2010 January 27.
23. Nakashima A, Ito M, Shima T, Bac N D, Hidaka T, Saito S. Accumulation of IL-17-positive cells in decidua of inevitable abortion cases. Am J Reprod Immunol. 2010 Jul. 1; 64(1):4-11. Epub 2010 Mar. 4.
24. Bansal A S. Joining the immunological dots in recurrent miscarriage. Am J Reprod Immunol. 2010 November; 64(5):307-15. doi:10.1111/j.1600-0897.2010.00864.x. Review.
25. Saito S, Nakashima A, Shima T, Ito M. Th1/Th2/Th17 and regulatory T-cell paradigm in pregnancy. Am J Reprod Immunol. 2010 June; 63(6):601-10. Epub 2010 Apr. 23. Review.
26. Bansal A S, Bajardeen B, Shehata H, Thum M Y. Recurrent miscarriage and autoimmunity. Expert Rev Clin Immunol. 2011 January; 7(1):37-44. Review.
27. Wakashin H, Hirose K, Iwamoto I, Nakajima H. Role of IL-23-Th17 cell axis in allergic airway inflammation. Int Arch Allergy Immunol. 2009; 149 Suppl 1:108-12. Epub 2009 Jun. 3. Review.
28. Cardoso C R, Garlet G P, Crippa G E, Rosa A L, Junior W M, Rossi M A, Silva J S. Evidence of the presence of T helper type 17 cells in chronic lesions of human periodontal disease. Oral Microbiol Immunol. 2009 February; 24(1):1-6.
29. Duerr R H, Taylor K D, Brant S R, Rioux J D, Silverberg M S, Daly M J, Steinhart A H, Abraham C, Regueiro M, Griffiths A, Dassopoulos T, Bitton A, Yang H, Targan S, Datta L W, Kistner E O, Schumm L P, Lee A T, Gregersen P K, Barmada M M, Rotter J I, Nicolae D L, Cho J H. A genome-wide association study identifies IL-23R as an inflammatory bowel disease gene. Science. 2006 Dec. 1; 314(5804):1461-3. Epub 2006 Oct. 26.
30. Cargill M, Schrodi S J, Chang M, Garcia V E, Brandon R, Callis K P, Matsunami N, Ardlie K G, Civello D, Catanese J J, Leong D U, Panko J M, McAllister L B, Hansen C B, Papenfuss J, Prescott S M, White T J, Leppert M F, Krueger G G, Begovich A B. A large-scale genetic association study confirms IL-12B and leads to the identification of IL-23R as psoriasis-risk genes. Am J Hum Genet. 2007 February; 80(2):273-90. Epub 2006 Dec. 21.

What is claimed is:

1. A method for detecting a soluble Δ9 isoform of the human IL-23 receptor (IL-23Rα) in a biological sample, wherein said Δ9 isoform consists of the amino acid sequence of SEQ ID NO:2, the method comprising the steps of:
   (a) obtaining a biological sample;
   (b) immobilizing on a solid support with a capture reagent, said capture reagent comprises a first antibody that binds to said soluble Δ9 isoform of the human IL-23Rα at the amino acid residues 318-348 of SEQ ID NO:2;
   (c) incubating said biological sample with said immobilized capture reagent to allow said soluble Δ9 isoform of IL-23Rα to bind to said immobilized capture reagent;
   (d) incubating a second antibody that binds to the extracellular domain of the human IL-23Rα and is coupled with a detecting agent, to allow said second antibody to bind to the captured soluble Δ9 isoform of IL-23Rα;
   (e) washing said solid support; and
   (f) adding a detectable reagent to detect the signal generated by the bound second antibody.

2. The method of claim 1, wherein said first antibody is a monoclonal antibody.

3. The method of claim 2, wherein said second antibody is a polyclonal antibody.

4. The method of claim 1, wherein said biological sample is selected from the group consisting of blood and plasma, wherein said biological sample comprising EDTA.

5. The method of claim 4, wherein said biological sample is EDTA-treated plasma.

6. The method of claim 1, wherein the incubating step (c) is performed at a pH of about 6.0 to about 10.0.

7. The method of claim 1, wherein the incubating step (c) is performed at a pH of about 9.5.

8. The method of claim 1, wherein the incubating step (c) is performed at a temperature of about 0° C. to about 25° C.

9. The method of claim 1, wherein the incubating step (c) is performed at a temperature of about 4° C.

10. The method of claim 1, wherein the incubating step (c) is performed for about 0.5 to about 3.0 hours.

11. The method of claim 1, wherein the incubating step (c) is performed for about 3.0 hours.

12. The method of claim 1, wherein said detectable reagent is streptavidin-HRP.

* * * * *